(12) United States Patent
Kao et al.

(10) Patent No.: US 10,138,282 B2
(45) Date of Patent: Nov. 27, 2018

(54) PEPTIDE ANTAGONIST OF LL-37

(71) Applicants: INDIANA UNIVERSITY RESEARCH AND TECHNOLOGY CORPORATION, Indianapolis, IN (US); JANSSEN BIOTECH, INC., Horsham, PA (US)

(72) Inventors: C. Cheng Kao, Bloomington, IN (US); Divyendu Singh, Bloomington, IN (US); Lani Rose San Mateo, Devon, PA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/312,027

(22) PCT Filed: May 21, 2015

(86) PCT No.: PCT/US2015/031928
§ 371 (c)(1),
(2) Date: Nov. 17, 2016

(87) PCT Pub. No.: WO2015/183683
PCT Pub. Date: Dec. 3, 2015

(65) Prior Publication Data
US 2017/0081378 A1    Mar. 23, 2017

Related U.S. Application Data

(60) Provisional application No. 62/003,118, filed on May 27, 2014.

(51) Int. Cl.
| | | |
|---|---|---|
| C07K 14/47 | (2006.01) |
| A61K 38/17 | (2006.01) |
| A61K 31/505 | (2006.01) |
| A61K 31/7036 | (2006.01) |
| A61K 31/704 | (2006.01) |
| A61K 45/06 | (2006.01) |

(52) U.S. Cl.
CPC ........ *C07K 14/4723* (2013.01); *A61K 31/505* (2013.01); *A61K 31/704* (2013.01); *A61K 31/7036* (2013.01); *A61K 38/1729* (2013.01); *A61K 45/06* (2013.01)

(58) Field of Classification Search
CPC .. A61K 38/1729; A61K 45/06; A61K 31/505; A61K 31/7036; A61K 31/704; A61K 2300/00; C07K 14/4723
See application file for complete search history.

(56) References Cited

U.S. PATENT DOCUMENTS

2007/0065908 A1    3/2007  Gallo et al.
2009/0088382 A1*   4/2009  Stahle-Backdahl .......... A61K 9/1272
                                                    514/1.1
2012/0315290 A1   12/2012  Gilliet et al.
2013/0287839 A1   10/2013  Stahle-Backdahl et al.
2014/0017787 A1    1/2014  Betancourt

FOREIGN PATENT DOCUMENTS

WO     WO-2010091294 A2 *   8/2010    ............. A01N 37/46

OTHER PUBLICATIONS

Brogden et al, Antimicrobial peptides in animals and their role in host defences, International Journal of Antimicrobial Agents, 2003, 22, pp. 465-478.*
Bagella et al, cDNA sequences of three sheep myeloid cathelicidins, FEBS Letters, 1995, 376, pp. 225-228.*
Nan et al, Prokaryotic selectivity and LPS-neutralizing activity of short antimicrobial peptides designed from the human antimicrobial peptide LL-37, Peptides, 2012, 35, pp. 239-247.*
Svensson et al, LL-37-induced host cell cytotoxicity depends on cellular expression of the globular C1q receptor (p33), Biochem. J., 2016, 473, pp. 87-98.*
Di, Strategic Approaches to Optimizing Peptide ADME Properties, The AAPS Journal, 2015, 17, pp. 134-143.*
Thayer, Improving Peptides, from https://pubs.acs.org/cen/coverstory/89/8922cover.html, May 30, 2011, pp. 1-7.*
Arcidiacono et al, Cy5 labeled antimicrobial peptides for enhanced detection of *Escherichia coli* 0157:H7, Biosensors and Bioelectronics, 2008, 23, pp. 1721-1727.*
Weber et al, A Fast and Inexpensive Method for N-Terminal Fluorescein-Labeling of Peptides, Bioorganic & Medicinal Chemistry Letters,1998, 8, pp. 597-600.*
12 Strongest Natural Antibiotics, Backed by Science, from https://www.superfoodly.com/strongest-natural-antibiotics/, Sep. 12, 2017, pp. 1-20.*
Kanamycin, from https://www.drugbank.ca/drugs/DB01172, pp. 1-9, accessed Mar. 23, 2018.*
Naghmouchi et al, Antibiotic and antimicrobial peptide combinations: synergistic inhibition of Pseudomonas fluorescens and antibiotic-resistant variants, Research in Microbiology, 2012, 163, pp. 101-108.*
Nan, Yong Hai, et al. "Prokaryotic selectivity and LPS-neutralizing activity of short antimicrobial peptides designed from the human antimicrobial peptide LL-37." Peptides 35.2 (2012):239-247.
Bolte S., et al., "A guided tour into subcellular colocalization analysis in light microscopy." J. Microsc. 224, 213-232 (2006).
Elssner A., et al. "A novel P2X7 receptor activator, the human cathelicidin-derived peptide LL37, induces IL-1b processing and release." J. Immunol. 172: 4987-4994 (2004).
Johansson J., et al. "Conformation-dependent antibacterial activity of the naturally occurring human peptide LL-37." J. Biol. Chem. 273, 3718-3724 (1998).
Kawai, T., et al. "TLR Signaling", Cell Death and Differentiation (2006) 13, 816-825.

(Continued)

Primary Examiner — Julie Ha
Assistant Examiner — Li N Komatsu
(74) *Attorney, Agent, or Firm* — Barnes & Thornburg LLP

(57) ABSTRACT

This disclosure is related to the peptide antagonist of LL-37, an antimicrobial peptide that has multiple functions in both innate and adaptive immune response. Specifically, the identified peptide antagonists of LL-37 provide inhibition to detrimental autoimmune inflammatory response, whereas at the same time retain LL-37's antibacterial activity.

5 Claims, 15 Drawing Sheets
Specification includes a Sequence Listing.

(56) References Cited

OTHER PUBLICATIONS

Kahlenberg M., et al. "Little Peptide, Big Effects: the role of LL-37 in inflammation and Autoimmune Disease." J. Immunol. 2013; 191: 4895-4901.

Kahlenberg, J., et al. "Neutrophil extracellular trap-associated protein activation of the NLRP3 inflammasome is enhanced in lupus macrophages." J. Immunol. 190: 1217-1226 (2013).

Lai Y., et al. "Viral double-strand RNA-binding proteins can enhance innate immune signaling by toll-like Receptor 3." PLoS ONE vol. 6, Issue 10, e25837, 13 pages (2011).

Scott M.G., et al. "The human antimicrobial peptide LL-37 is a multifunctional modulator of innate immune responses." J. Immunol. 169: 3883-3891 (2002).

Sekar R. B., et al. "Fluorescence resonance energy transfer (FRET) microscopy imaging of live cell protein localizations." J. Cell Biol. 160, 629-633 (2003).

Singh D., et al. "The human antimicrobial peptide LL-37, but not the mouse ortholog, mCRAMP, can stimulate signaling by poly(I:C) through a FPRL1-dependent pathway." J. Biol. Chem. 288, 8258-8268 (2013).

Vaughan R., et al. "Identification and functional characterization of the nascent RNA contacting residues of the hepatitis C virus RNA-dependent RNA polymerase." RNA 18, 1541-1552 (2012).

PCT Search Report and Written Opinion completed on 22OCT5 and issued in connection with PCT/US2015/031928, dated Nov. 24, 2015, 13 pages.

\* cited by examiner

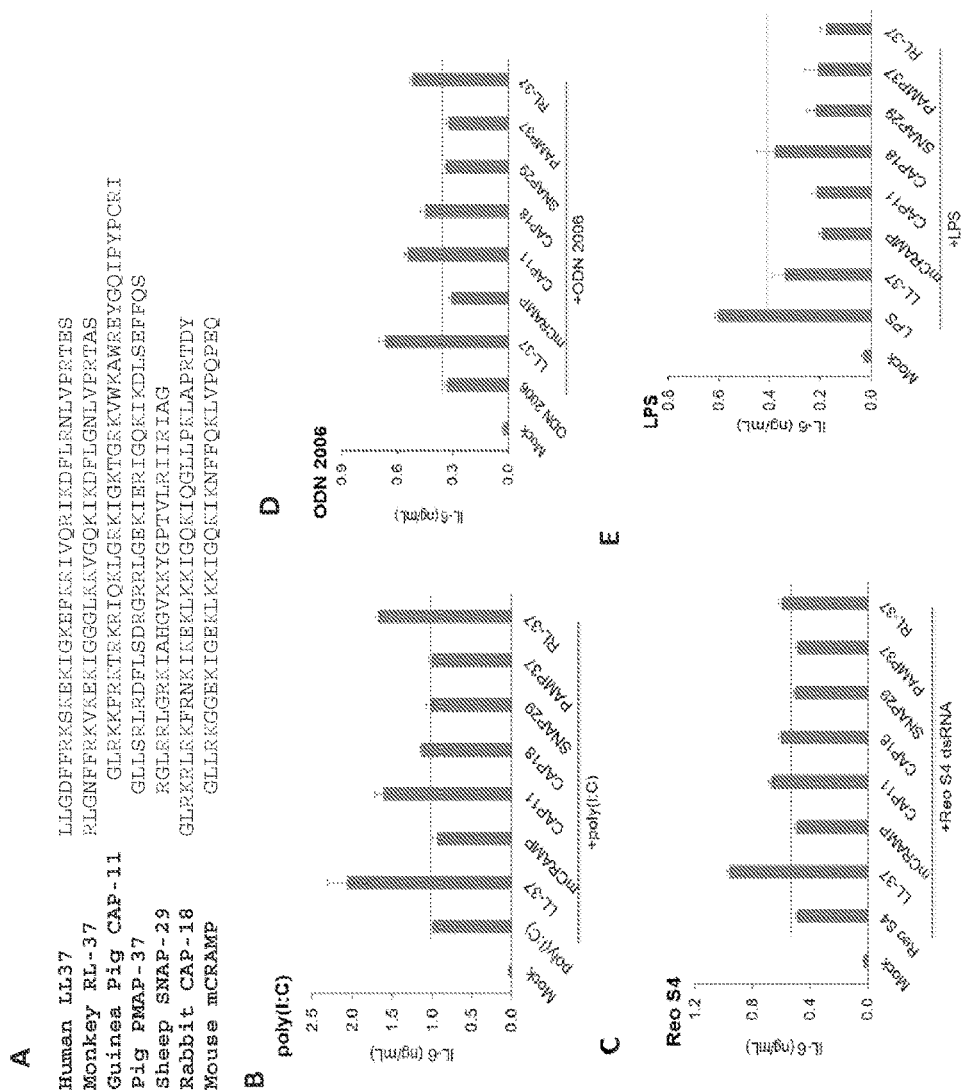

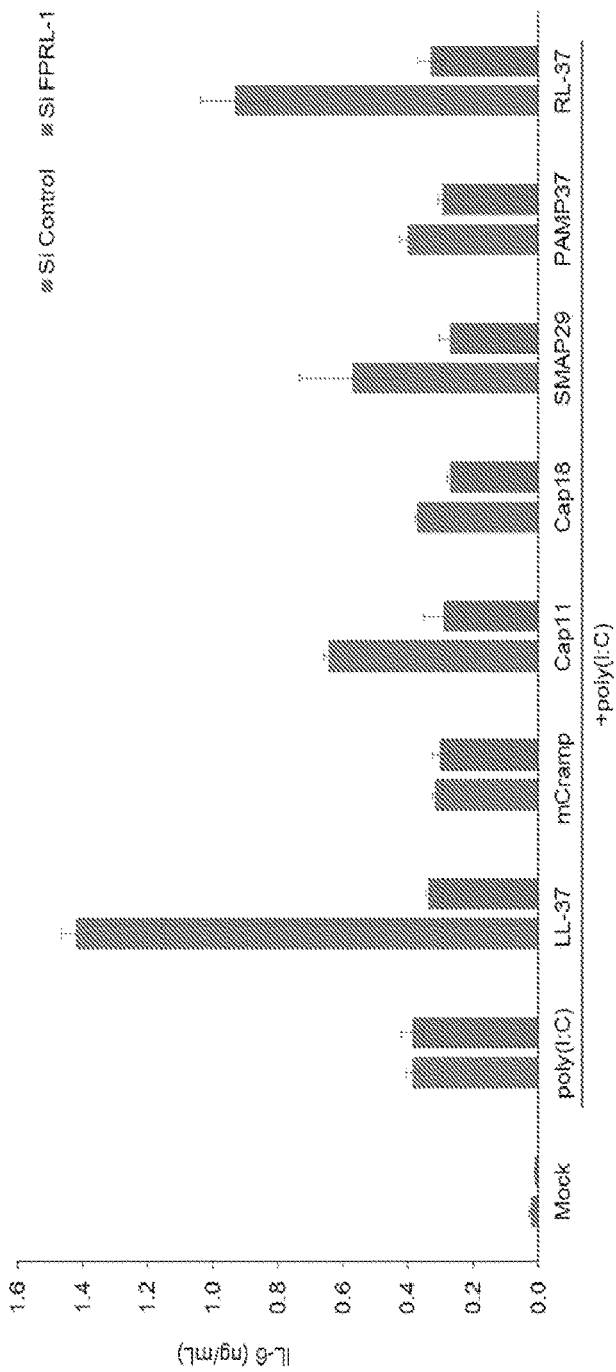

PEPTIDE ANTAGONIST OF LL-37

CROSS REFERENCE

This application is a national stage entry under 35 USC § 371(b) of PCT International Application No. PCT/US2015/031928, filed May 21, 2015, and claims the benefit under 35 USC § 119(e) to U.S. Provisional Patent Application No. 62/003,118, filed May 27, 2014, the disclosures of which are expressly incorporated by reference in their entirety.

SEQUENCE LISTING

The instant application contains a Sequence Listing which has been submitted electronically in ASCII format and is hereby incorporated by reference in its entirety. Said ASCII copy, created on Jan. 31, 2018, is named 29920-260130_SL.txt and is 8,386 bytes in size.

FIELD OF THE INVENTION

This disclosure is related to the peptide antagonist of LL-37, an antimicrobial peptide that has multiple functions in both innate and adaptive immune response. Specifically, the identified peptide antagonists of LL-37 and LL-37 orthologs from other mammals provide inhibition to detrimental autoimmune inflammatory responses, whereas at the same time retain LL-37's antibacterial activity.

BACKGROUND

LL-37 is a multifunctional 37-residue antimicrobial peptide produced by human epithelial cells and immune cells by proteolytic cleavage from the C-terminal portion of the hCAP-18 protein. The 18-kDa hCAP18 is synthesized and stored in granules and lamellar bodies. Following stimulation by proinflammatory signals, hCAP18 is released into the extracellular environment and cleaved by proteinase 3 in neutrophils and kallikrein in keratinocytes and the N-terminal 37 amino acid form the alpha-helical LL-37 peptide that then forms higher order oligomers in solution.

Unlike other antimicrobial peptides, LL-37 is protected from proteolytic degradation. Its positive charge allows it to preferentially associate with negatively charged phospholipid membranes. Furthermore, it assumes a primarily alpha-helical shape during membrane interactions, resulting in unilateral segregation of its hydrophobic residues. This allows for membrane penetration, formation of transmembrane pores, and bacterial death by leakage of bacterial cell contents.

In addition to LL-37's ability to kill bacteria, it can also regulate the activities of multiple innate immune receptors. High levels of LL-37 are associated with autoimmune diseases such as psoriasis, systemic lupus erythromatosis, and asthma, suggesting that overexpression of LL-37 could be linked to diseases.

Indeed, both pro- and anti-inflammatory functions have been assigned to LL-37 and these activities may be modulated by the microenvironment and disease.

Exposure to LL-37 results in recruitment of inflammatory cells, induction of M1 macrophages, and stimulation of inflammatory responses such as inflammasome activation and type I IFN production. For example, LL-37 influences inflammatory cell recruitment and macrophage phenotype.

However, LL-37 also has strong anti-inflammatory effects such as neutralization of TLR4 signal transduction in response to lipopolysaccharides (LPS; also known as endotoxin), down modulation of inflammatory cytokine responses, and preventing inflammatory responses to pathogenic bacteria.

It is understood that the Toll-like receptor (TLR) family plays an instructive role in innate immune responses against microbial pathogens, as well as the subsequent induction of adaptive immune responses. TLRs recognize specific molecular patterns found in a broad range of bacterial and viral pathogens, triggering inflammatory and antiviral responses, as well as dendritic cell maturation, which result in the eradication of invading pathogens. A thorough review of TLR signaling by T. Kawai et al. can be found in Cell Death and Differentiation (2006) 13, 816-825.

Dysregulation of TLR signaling has been reported to be important for the development of autoimmunity. Modulation of TLR function by LL-37 can be considered an anti-inflammatory effect. For example, LL-37 down-regulates signaling through TLR4 via binding of its ligand, LPS, as well as through interruption of TLR4 receptor complex function in dendritic cells (DCs) and macrophages. This results in lower levels of proinflammatory cytokine production when LL-37 and LPS are present simultaneously (see M Kahlenberg et al.: Little Peptide, Big Effects: the role of LL-37 in inflammation and Autoimmune Disease, J. Immunol. 2013; 191: 4895-4901)

Thus, based on the current knowledge on LL-37's role played in autoimmune diseases, and its potential to suppress inflammatory response, a balanced approach to better use LL-37 is desired. This disclosure identifies several antagonists of LL-37 and provides such advantages compared to other conventional compound selection of LL-37 antagonists.

SUMMARY

This disclosure provides the identification and activity of peptide antagonist for LL-37, an antimicrobial peptide involved in autoimmune diseases and immune regulation. Residues in LL-37 that contact poly (I:C) and facilitate oligomerization between LL-37 subunits in vitro were mapped and peptides antagonizing LL-37 were identified. The peptide antagonist inhibits autoimmune inflammatory responses induced by bacterial endotoxins, double-strand RNAs from viruses, or single-strand DNAs. These peptide antagonists retain or enhance LL-37's antibacterial activity, bind to LL-37 and/or bacterial endotoxin, but fail to bind double-stranded RNAs or single-strand DNAs.

These LL-37 antagonists include at least SEQ ID NO: 1(LL-29), SEQ ID NO: 2 (Peptide A), and SEQ ID NO: 3 (LL8-37). Further investigation of other mammal peptides identified several LL-37 orthologs such as SEQ ID NO: 22 (pig PAMP-37), SEQ ID NO: 23 (sheep SMAP-29) and SEQ ID NO: 24 (rabbit CAP-18) etc. These peptides, similar to the LL-37 analogs, failed to activate signaling by nucleic acids, yet retain native LL-37's antibacterial activity.

In some preferred embodiments, the aforementioned selected LL-37 antagonist is a composition consisting of adducts that covalently modified peptide. Adduct modified peptide nevertheless inhibits autoimmune inflammatory responses induced by bacterial endotoxins, double-stranded RNAs or single-stranded DNAs but retains antibacterial activity. Said adducts provide stabilized peptide that binds to LL-37 and/or endotoxins, but fails to bind double-stranded RNA or single-stranded DNA.

In some preferred embodiments, the aforementioned adducts are covalently added to the backbone of the peptide and convey additional activities to the peptide. For example, adducts can be fluorophores, other amino acids, peptides or antibiotics.

In some preferred embodiment, the aforementioned LL-37 antagonist is used in combination with antibiotics to treat bacterial infection. The combination inhibits inflammatory responses to bacterial endotoxins and improves the killing of the bacteria. The enhancement of the effects of the antibiotics will lead to reduced use of antibiotics in therapy. For example, LL-37 antagonist may reduce the concentration of antibiotics necessary to kill Gram-negative bacteria.

In one preferred embodiment, the selected LL-37 antagonist abrogates native LL-37 associated double-stranded nucleic acid trafficking to endosomes.

In aforementioned native LL-37/double-stranded nucleic acid complex, the trafficking to endosome is mediated by the formyl peptide receptor-like receptor-1 (FPRL-1).

In one preferred embodiment, the selected LL-37 antagonist inhibits TLR3-mediated autoimmune inflammatory response.

In one preferred embodiment, the selected LL-37 antagonist retains native LL-37's suppression of TLR4 signaling.

In one preferred embodiment, the selected LL-37 antagonist composition is SEQ ID NO: 1.

In one preferred embodiment, the selected LL-37 antagonists sequester TLR4 signaling molecule LPS or its equivalents.

This disclosure also provides a method to prevent native LL-37 enhanced autoimmune inflammatory response and retain native LL-37's antibacterial activity in a living subject. The method comprising:
  a. Identifying a composition of LL-37 antagonist that inhibits autoimmune inflammatory responses induced by bacterial endotoxins, double-stranded RNAs from viruses, or single-stranded DNAs. These peptide antagonists retain or enhance LL-37's antibacterial activity, bind to LL-37 and/or endotoxin, but fail to have the normal activities of binding double-stranded RNAs or single-stranded DNAs; and
  b. Providing the selected LL-37 antagonist in a ratio to native LL-37 sufficient to abrogate native LL-37 associated double-stranded nucleic acid trafficking to endosomes.

In some embodiment, the aforementioned method comprising peptide selected from the group of SEQ ID NO: 1(LL-29), SEQ ID NO: 2 (Peptide A), SEQ ID NO: 3 (LL8-37), SEQ ID NO: 22 (pig PAMP-37), SEQ ID NO: 23 (sheep SMAP-29) and SEQ ID NO: 24 (rabbit CAP-18) etc.

In one embodiment, the aforementioned method inhibits native LL-37 enhanced autoimmune inflammatory response mediated by TLR3. In another embodiment, the aforementioned method decouples native LL-37 associated double-stranded nucleic acid complex's trafficking to endosomes, which is mediated by FPRL-1.

In one embodiment, the aforementioned method retains native LL-37's suppression of TLR4 signaling by sequestering TLR4 signaling molecule LPS or its equivalents.

This disclosure further provides a peptide that is inhibitory to LL-37 induced inflammatory response, and enhances antimicrobial activity of antibiotics. The peptide preferably comprises an amino acid sequence that is at least 95% identity to SEQ ID NO:1 (LL-29).

The disclosure further discloses a peptide that reduces IL-6 production. Such peptide is selected from the group consisting of SEQ ID NO:1 (LL-29), SEQ ID NO: 2 (Peptide A), SEQ ID NO: 3 (LL8-37), SEQ ID NO:6 (mCRAMP), SEQ ID NO:20 (Monkey RL-37), SEQ ID NO:21 (Guinea pig CAP-11), SEQ ID NO: 22 (pig PAMP-37), SEQ ID NO: 23 (sheep SMAP-29) and SEQ ID NO: 24 (Rabbit CAP-18).

These and other features, aspects and advantages of the present invention will become better understood with reference to the following figures, associated descriptions and claims.

BRIEF DESCRIPTION OF FIGURES

FIG. 1A discloses SEQ ID NOS 4, 25, and 26, respectively, in order of appearance. B) Fluorescent polarization assay for LL-37 in the presence of increasing concentrations of the artificial double-stranded RNA, poly(I:C), in buffers at different pHs. LL-37 with an adduct composed of a fluorophore, fLL-37 was present in the assay at 0.1 µM and titrated with increasing concentration of unlabeled poly (I:C). C) Fluorescence polarization assay performed with fSc-37. fSc-37 was present in the assay at 0.1 µM and titrated with increasing concentrations of poly(I:C). D. Difference in fluorescent polarization of fLL-37 (0.1 µM) in the presence of different ligands at pH 7.4 and pH 6.2. fSc-37 was used as control. All data are the mean of three independent experiments. p values were determined using the Student t-test.

FIG. 5B discloses SEQ ID NOS 8-19, respectively, in order of appearance. C) Schematic of the regions within LL-37 that contact poly(I:C). The lines denote sequences of peptides identified to co-precipitate with poly(I:C). FIG. 5C discloses SEQ ID NO: 4.

FIG. 9 discloses SEQ ID NOS 6, 4, 7, 2, 1, 5, and 3, respectively, in order of appearance.

FIG. 14. Additional antimicrobial peptides, LL-37 orthologs, that retain the ability to suppress bacterial lipopolysaccharide-induced inflammatory cytokine production without activating nucleic acid-induced inflammatory cytokine production: A) Names and sequences of the LL-37 orthologs from various mammal species. FIG. 14A discloses SEQ ID NOS 4, 20-24, and 6, respectively, in order of appearance. B) The activation of IL-6 production in the human lung epithelial BEAS-2B cells by the 1 mM final concentration of the LL-37 orthologs in the presence of poly(I:C). IL-6 concentrations in the cell culture media 20 h after the addition of ligands were determined by ELISA. The IL-6 produced by BEAS-2B cells in the presence of the viral double-stranded RNA S4 from Reovirus. (C), the single-stranded DNA ODN2006 (D), and LPS (E) were determined by the same protocol.

FIG. 15. Antimicrobial peptides that are LL-37 orthologs have reduced activation of IL-6 production in response to viral nucleic acids have reduced usage of the formyl peptide receptor like-1 receptor. The expression of the FPRL-1 receptor in human lung epithelial BEAS-2B cells was knocked down using 30 nM of the siRNAs specific to FPRL-1. The knockdown was determined using qRT-PCR to be 70%. The amount of IL-6 in the culture media of the BEAS-2B cells was determined 20 h after the addition of the ligands poly(I:C) (0.3 mg/ml) and the peptides (1 mM). FIG. 15 discloses SEQ ID NOS 4, 20-24, and 6, respectively, in order of appearance.

BRIEF DESCRIPTION OF SEQUENCE LISTINGS

Figure 1:
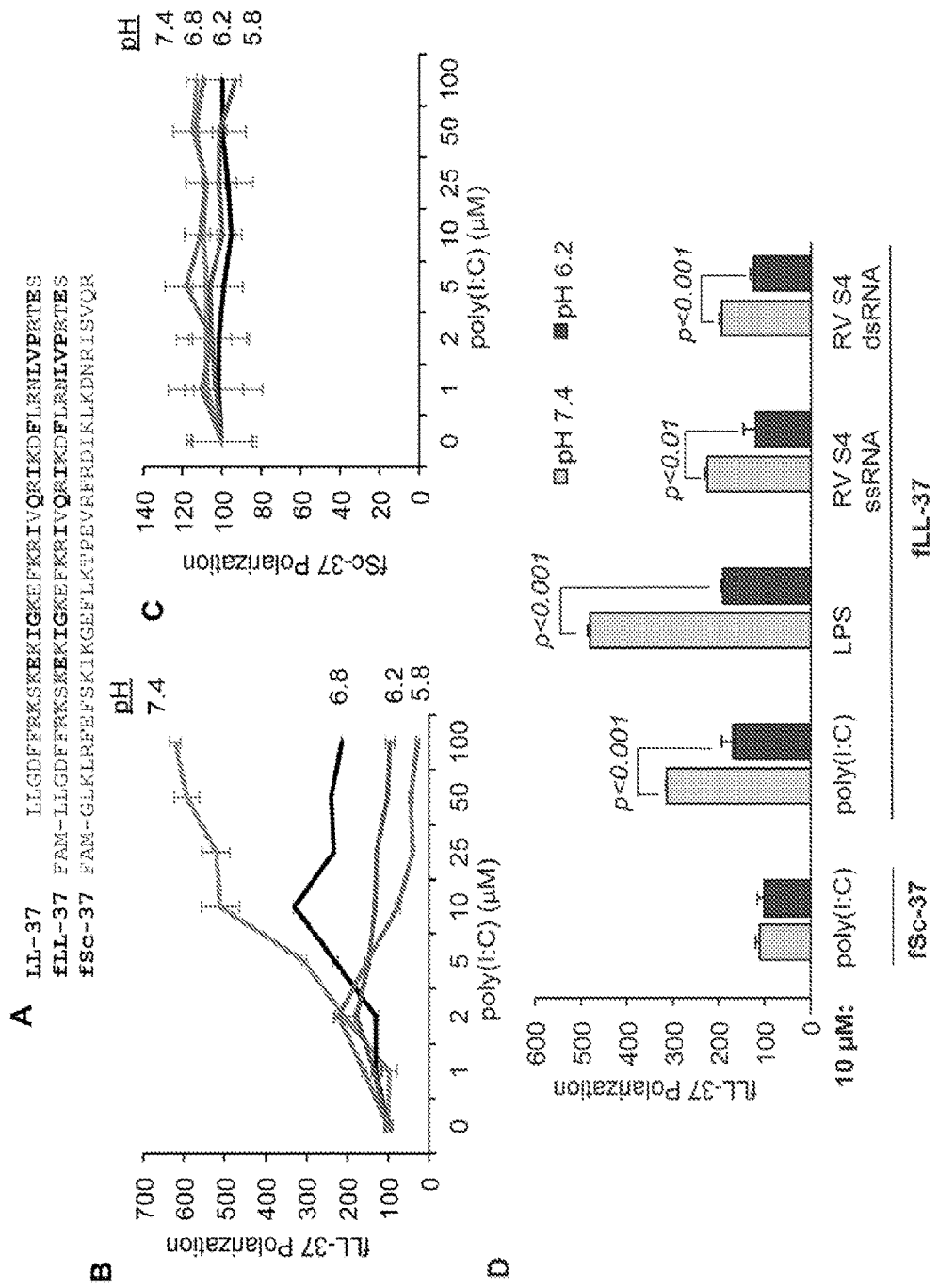
FIG. 1. Fluorescent polarization of LL-37 changes in the presence of ligands are pH dependent. A) Sequence of human antimicrobial peptide LL-37 and the scrambled peptide Sc-37.

SEQ ID NO: 1 is amino acid sequence of LL-29
SEQ ID NO: 2 is amino acid sequence of Peptide A
SEQ ID NO: 3 is amino acid sequence of LL8-37
SEQ ID NO: 4 is amino acid sequence of LL-37
SEQ ID NO: 5 is amino acid sequence of LL9-29
SEQ ID NO: 6 is amino acid sequence of pentamide
SEQ ID NO: 7 is amino acid sequence of mCRAMP
SEQ ID NOs: 8-19 are amino acid sequences of various portions of LL-37
SEQ ID NO: 8 is amino acid sequence 1-7 of LL-37
SEQ ID NO: 9 is amino acid sequence 1-8 of LL-37
SEQ ID NO: 10 is amino acid sequence 1-10 of LL-37
SEQ ID NO: 11 is amino acid sequence 1-12 of LL-37
SEQ ID NO: 12 is amino acid sequence 1-18 of LL-37
SEQ ID NO: 13 is amino acid sequence 1-19 of LL-37
SEQ ID NO: 14 is amino acid sequence 1-23 of LL-37
SEQ ID NO: 15 is amino acid sequence 13-19 of LL-37
SEQ ID NO: 16 is amino acid sequence 20-29 of LL-37
SEQ ID NO: 17 is amino acid sequence 24-34 of LL-37
SEQ ID NO: 18 is amino acid sequence 24-37 of LL-37
SEQ ID NO: 19 is amino acid sequence 30-37 of LL-37
SEQ ID NO: 20 is amino acid sequence of Monkey RL-37
SEQ ID NO: 21 is amino acid sequence of Guinea Pig CAP-11
SEQ ID NO: 22 is amino acid sequence of pig PMAP-37
SEQ ID NO: 23 is amino acid sequence of Sheep SMAP-29
SEQ ID NO: 24 is amino acid sequence of Rabbit CAP-18

DETAILED DESCRIPTION AND PREFERRED EMBODIMENT

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person with ordinary skill in the art pertaining to this disclosure.

The innate immune system plays a crucial role in defense against microbes as well as in the initiation of inflammatory responses. Antimicrobial peptides (AMPs) are an important evolutionarily conserved defense mechanism against bacterial and fungal invasion of eukaryotic organisms. Hundreds of AMPs are synthesized by epithelial cells and lymphocytes. Although several classes of AMPs exist, LL-37 is the sole member of the human cathelicidin family. This peptide has piqued the interest of the research community because, in addition to its antimicrobial properties, it carries numerous immune system—modulating properties that may contribute to autoimmune disease development (M. Kahlenberg et al.: Little peptide, big effects: the role of LL-37 in inflammation and autoimmune disease, *J. Immunol.* 2013; 191: 4895-4901)

Toll-like receptors (TLRs) are widely expressed receptors that respond to pathogen associated molecular patterns. Depending on the sequence of LL-37 and LPS exposure, the effects of LL-37 on TLR4 responses can be proinflammatory. It is reported when macrophages are primed with LPS prior to LL-37 exposure, there is enhanced release of TNF-α (M. G. Scott et al. 2002. The human antimicrobial peptide LL-37 is a multifunctional modulator of innate immune responses. *J. Immunol.* 169: 3883-3891).

Furthermore, LPS priming of monocytes and macrophages allows for activation of the inflammasome and production of inflammation-promoting cytokines such as IL-1β and IL-6 production following LL-37 stimulation. See J. Kahlenberg, et al. 2013: Neutrophil extracellular trap-associated protein activation of the NLRP3 inflammasome is enhanced in lupus macrophages. J. Immunol. 190: 1217-1226, and A. Elssner et al. 2004: A novel P2X7 receptor activator, the human cathelicidin-derived peptide LL37, induces IL-1b processing and release. *J. Immunol.* 172: 4987-4994.

The increased inflammatory response complicates LL-37's role in immune regulation. Prior research shows that mCRAMP (murine ortholog of LL-37) does not have an activity to stimulate TLR3. (Y. Lai et al. 2011: LL37 and cationic peptides enhance TLR3 signaling by viral double-stranded RNAs. PLoS ONE 6: e26632). However, mCRAMP retains LL-37's ability to suppress the inflammatory response against bacterial LPS. In the same article, the authors establish that LL-37 stabilizes TLR3 ligands and is able to enhance viral responses transmitted via this receptor in TLR3-transfected bronchial epithelial cells. In contrast, there is modulation of TLR3 responses in keratinocytes leading to repression of poly(I:C)-mediated upregulation of CXCL10 and CCL5 but enhancement of polyinosinic-polycytidylic acid-induced chemokine, CXCL8. These observations again support the concept that LL-37 can enhance or abrogate inflammatory signals depending on cell type, the LL-37 sequence, and the microenvironment.

Thus, the ability of LL-37 to have a suppressive effect on LPS effects depends on the timing, peptide sequence, and context within which cells are exposed. This disclosure provides an alternative mechanism to regulate LL-37 activity.

Briefly, in this disclosure we have elucidated the mechanism whereby LL-37 can differentially up-regulates the inflammatory response to nucleic acids and down-regulates the inflammatory response to bacterial endotoxin. We determined that LL-37 binds dsRNA and traffics to endosomes and releases the dsRNA in a pH-dependent manner. This release delivers dsRNA to TLR3 and up-regulates the inflammatory responses. TLR3 signals from endosomes and its binding to dsRNA increases in affinity upon acidification of the endosomes. In contrast, TLR4 binding to bacteria endotoxin on the surface of cells and binding does not involve endosomes and endosome acidification. Thereby, LL-37 forms a stable complex to endotoxin and prevents the recognition of endotoxin by TLR4.

With regard to LL-37 recognition of dsRNA, we performed dynamic light scattering spectroscopy and cell-based Förster resonance energy transfer (FRET) experiments. LL-37 was found to form higher order complexes independent of dsRNA binding. Upon acidification LL-37 will dissociate from a larger complex. In cells, LL-37 has a half-live of ca. 1 h. LL-37 half-life was increased by inhibiting endosome acidification or inhibiting cathepsins, proteases whose activity is increased with endosome acidification. Finally, residues in LL-37 that contact poly(I:C) and facilitate oligomerization in vitro were mapped, and peptide LL-29 derived from LL-37 inhibited LL-37 enhancement of TLR3 signal transduction. LL-29 prevented delivery of dsRNA to endosomes with TLR3. Other derivatives of LL-37 which can serve as alternative LL-37 antagonists are discovered. Without being limited by any theory, these results shed light on the requirements for LL-37 enhancement of TLR3 signaling.

We determined that the pH of the environment could regulate LL-37 interaction with dsRNA both in solution and in cells. LL-37 binds the double-stranded RNA poly(I:C) at neutral pHs in vitro, and releases it when the pH decreases. Within cells, the release of dsRNA was measured by a loss of the Förster resonance energy transfer between molecules that contain fluorophores. Cells inhibited for endosome acidification retained the interaction between LL-37 and the dsRNA poly(I:C). LL-37 also exists in solution as a higher order complex that can dissociate upon acidification of the solution. These results are consistent with the observations that the oligomeric state of LL-37 and a neutral pH are needed for its function, and extend these requirements to the binding of dsRNA and activation of TLR3 signaling. A schematic for the effects of LL-37 on dsRNA signaling by TLR3 is presented in FIG. 8.

Without being limited by the theory, the pH-dependent binding and release of dsRNA by LL-37 explains the differential effects of LL-37 on TLR3 and TLR4 signaling. It is likely that LL-37 does not readily release LPS due to the binding occurring at neutral pHs. Thus, LL-37 can sequester LPS to prevent TLR4 signaling. In contrast, LL-37 traffics dsRNA to endosomes where it can be bound by TLR3 to activate signaling. It is important to note that dsRNA can traffic to endosomes independent of LL-37 through scavenger receptors. Indeed, TLR3 can signal in response to poly(I:C), albeit at a reduced level, even in the absence of LL-37. In the presence of LL-37, TLR3 signaling may be enhanced due to the increased concentrations of the dsRNA in endosomes where TLR3 is resident.

Figure 4:
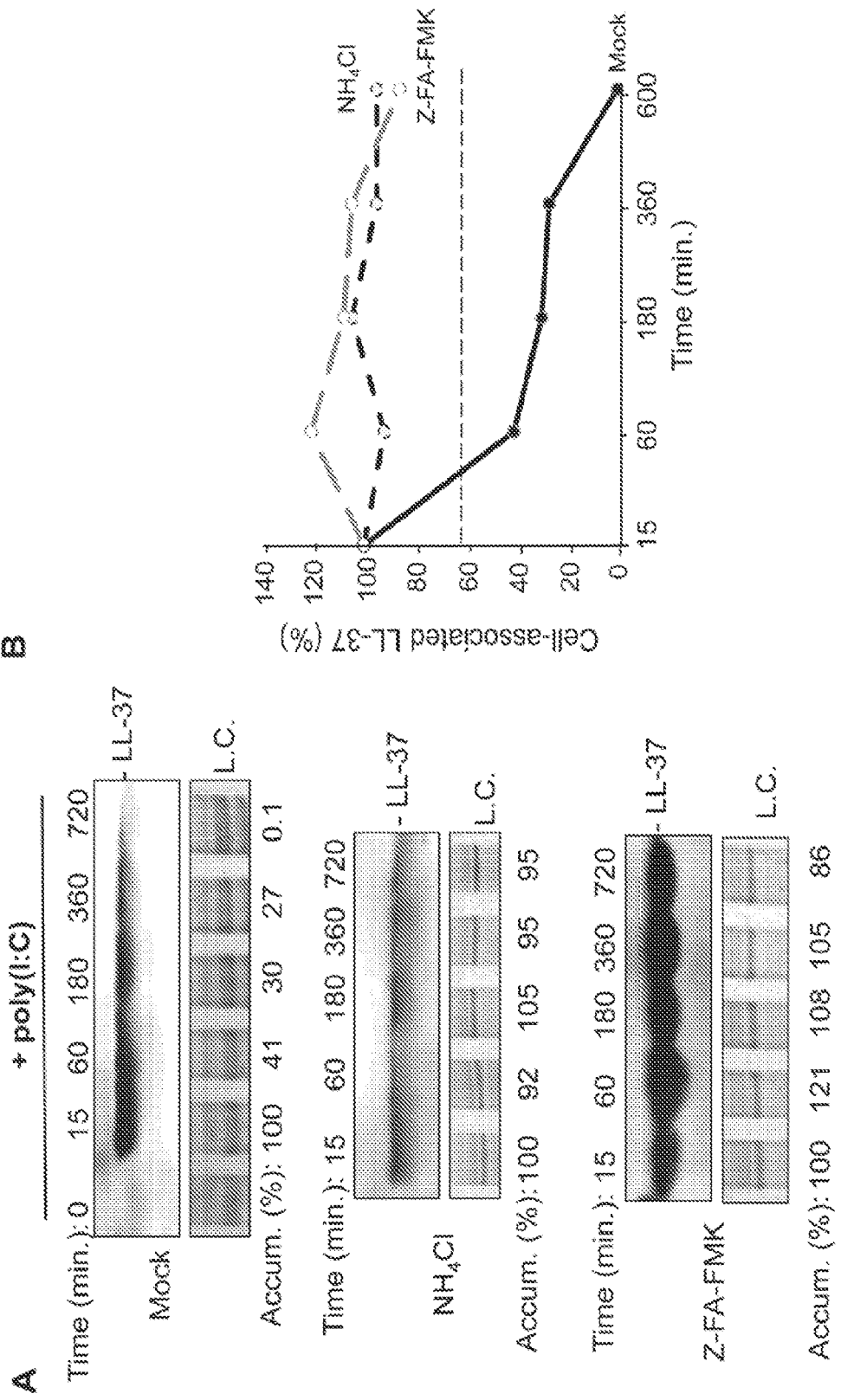
FIG. 4. LL-37 is degraded in endosomes of BEAS-2B cells. A) Western blot assessing the accumulation of LL-37 over time after its addition along with poly(I:C) (0.13 µg/mL) to BEAS-2B cells. Upper panel: Accumulation of LL-37 in untreated BEAS-2B cells. Middle panel: the accumulation of LL-37 in the presence of endosomal acidification inhibitor $NH_4Cl$ (5 µM final concentration). Bottom panel: the accumulation of LL-37 in the presence of cathepsin inhibitor Z-FA-FMK (5 µM final concentration). In all three panels LL-37 was detected by Western blot of cell lysates electrophoresed in NuPAGE 4-12% Bis-Tris gels designed to separate small proteins. Quantification of band intensity is calculated relative to that of the loading control (L.C.). B) Half-life of LL-37 as measured by band intensity of western blot with and without endosomal acidification inhibitor or a cathepsin inhibitor. A similar increase in LL-37 half-life was observed in two independent experiments.

Thus, without being limited by this theory, pH likely coordinates a number of consequential events for signaling by TLR3. Endosome acidification can also activate cathepsins, proteases to enhance the stability of signaling-competent TLR3 and trigger the degradation of LL-37 (FIG. 4). Notably, inhibition of endosome acidification, cathepsins B, L and/or S with the inhibitor Z-FA-FMK increased the half-life of LL-37 from 1 h to an excess of 12 h (FIG. 4B).

Figure 5:
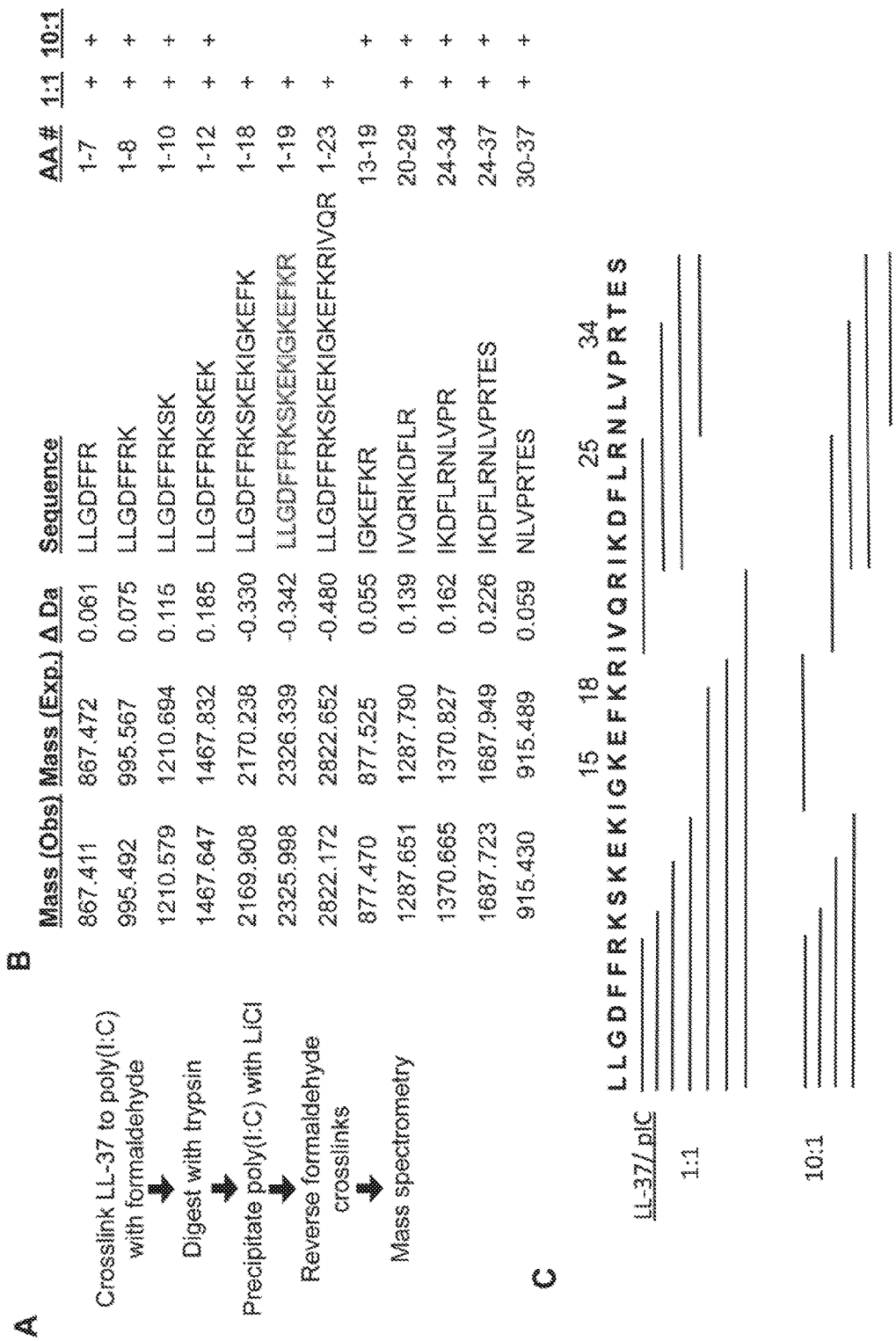
FIG. 5. Mapping of the LL-37 residues that contact poly(I:C). A) Schematic of the RCAP protocol. B) Summary of the peptides from LL-37 found to contact poly(I:C). Peptides identified mass spectrometry within an accuracy of 0.5 Da of the theoretical masses are denoted with a + symbol.

Despite its small size, LL-37 has numerous activities: binding to RNA, associate or dissociate as a function of pH, and trafficking to endosomes via the FPRL-1 receptor. Our characterization of LL-37 and variants contributes to how LL-37 residues participate in these activities. For RNA binding, the overall positive charge of LL-37 (11 positive residues out of 37) is not sufficient; both mCRAMP (9 positively-charged residues out of 34) and Pentamide (11 positively-charged residues out of 37) failed to bind dsRNA in our fluorescent polarization assay and failed to enhance TLR3 signaling (Table 1). The properties of Pentamide may be especially informative since it has the identical positively-charged residues as those in LL-37. Results from mapping studies suggest that the residues at the terminal regions of LL-37 preferentially contact dsRNA (FIG. 5). Consistent with this conclusion, Peptide A, which has the C-terminal four residues replaced with those from mCRAMP, was debilitated for binding RNA. Peptides lacking the N- and C-terminal residues of LL-37 were also defective for binding dsRNA and enhancing TLR3 signaling (Table 1). Table 1 discloses SEQ ID NOS 6, 4, 7, 2, 1, 5, and 3, respectively, in order of appearance.

TABLE 1

Summary of the activities of LL-37 and variants.

| Peptide | Sequence[1] | IL-6 production (%)[2] | | Hydrodynamic radius (nm)[3] | | Binding f-LL37[5] |
|---|---|---|---|---|---|---|
| | | LPS-depend. | poly(I:C)-depend. | pH 7.4 | pH 5.8 | |
| None | | | | | | |
| mCRAMP | GLLRKGGEKIGEKLKKIGQKIKNFFQKLVPQPEQ | 82 ± 29 | 31 ± 3 | 1718 | 1106 | 2.6 ± 0.3 |
| LL-37 | LLGDFFRKSKEKIGKEFKRIVQRIKDFLRNLVPRTES | 100 ± 14 | 100 ± 3 | 1356.2 | 4 | 6.0 ± 0.1 |
| Pentamide | LLGNFFRKSKQKIGKQFKRIVQRIKNFLRNLVPRTQS | 400 ± 32 | 31 ± 0 | 1106 | 1990 | ND |
| Peptide A | LLGDFFRKSKEKIGKEFKRIVQRIKDFLRKLVPQPEQ | 161 ± 11 | 41 ± 6 | 1990 | 956 | 5.0 ± 0.2 |
| LL29 | LLGDFFRKSKEKIGKEFKRIVQRIKDFLR-------- | 143 ± 18 | 47 ± 3 | 1106 | 8 | 6.2 ± 0.5 |

TABLE 1-continued

Summary of the activities of LL-37 and variants.

| Peptide | Sequence[1] | IL-6 production (%)[2] | | Hydrodynamic radius (nm)[3] | | Binding f-LL37[5] |
|---|---|---|---|---|---|---|
| | | LPS-depend. | poly(I:C)-depend. | pH 7.4 | pH 5.8 | |
| LL9-29 | --------SKEKIGKEFKRIVQRIKDFLR-------- | 196 ± 11 | 31 ± 3 | 446.5 | 1281 | 2.6 ± 0.2 |
| LL8-37 | --------SKEKIGKEFKRIVQRIKDFLRNLVPRTES | 239 ± 21 | 38 ± 3 | 825 | 615 | ND |

[1]Amino acid residues changed from LL-37 are in bold and underlined. The residues deleted from LL-37 are shown with a dash.
[2]IL-6 production in BEAS-2B cells induced with 1.0 µg/ml of LPS or 130 ng/ml of poly(I:C).
[3]Dynamic light scatter spectroscopy results determined with 1.0 µM of the peptides in Phasphate buffers adjusted to pH 7.4 or 5.8.
[4]Fold change in the fluorescence anisotropy values of f-LL-37 between 1.0 nM and 1000 nM of added peptide.

Truncated peptides derived from LL-37 were also informative for the interaction between LL-37 subunits. LL-29 can bind to LL-37 to the same extent that LL-37 can, indicating that the C-terminal eight residues of LL-37 are not required for the interaction between LL-37 peptides. We propose that the central ca. 20 residues of LL-37 likely anchor the interaction between LL-37 subunits. The N-terminal residues, at least some subunits of which contact dsRNA, likely contribute to subunit interaction since a deletion of the N-terminal 8 residues significantly reduced interaction with LL-37 (Table 1).

Figure 6:
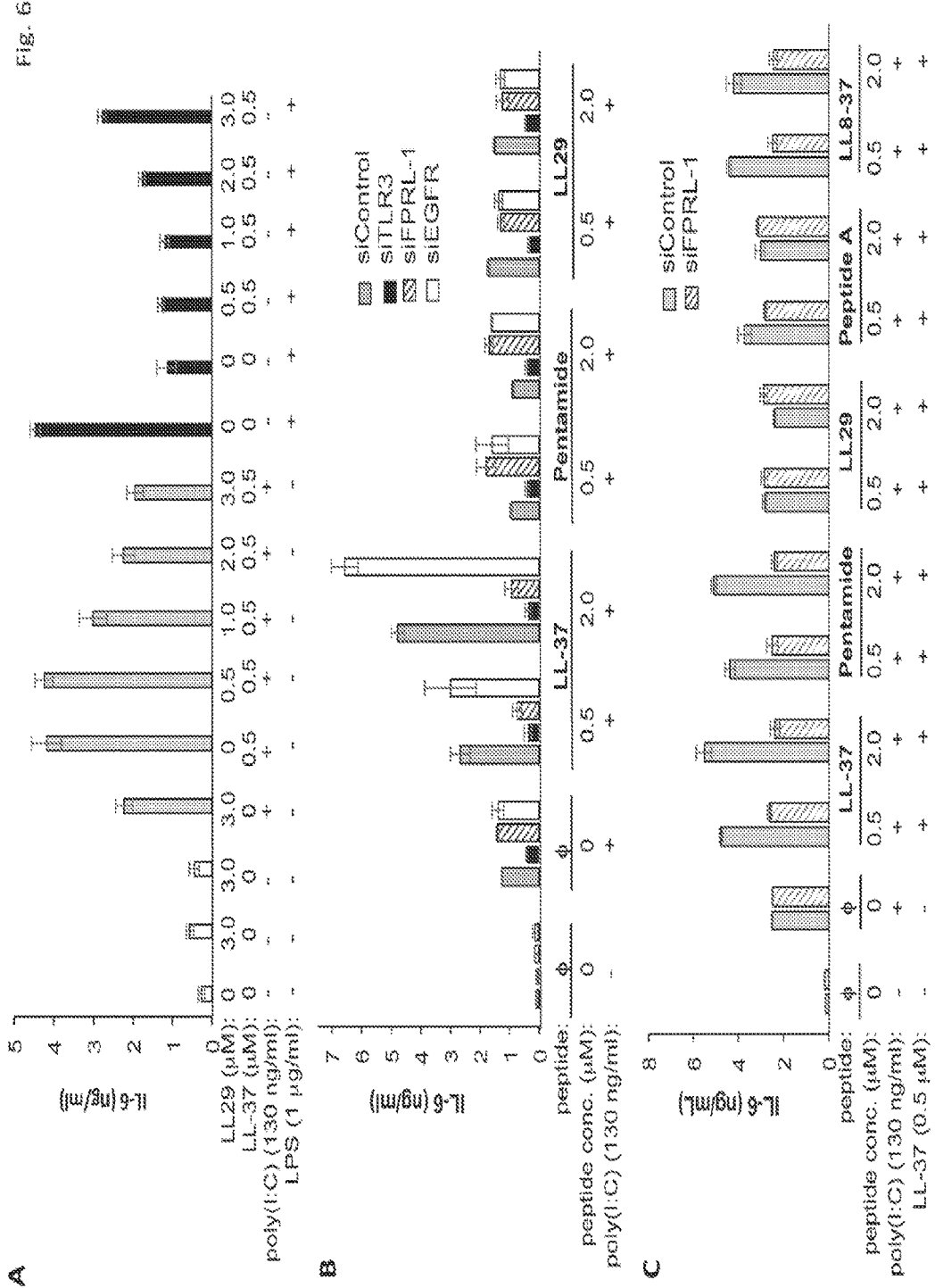
FIG. 6. Activities of truncated LL-37 peptides on LPS- and poly(I:C)-induced signaling. A) IL-6 production induced by LPS or poly(I:C) in BEAS-2B cells after addition of LL-37 in presence or absence of LL-29 peptides. The final concentrations of the peptides are shown below the graph. The addition of poly(I:C) (to 130 ng/ml) or LPS (to 1 µg/ml) are denoted by a "+" symbol. All samples were performed in at least triplicates and the results are representative of three independent experiments. B) LL-29 does not enhance TLR3 signaling through the Formyl peptide receptor-like receptor-1 (FPRL-1). TLR3 signaling was assessed by measuring IL-6 levels in BEAS-2B cells knocked down with TLR3, FPRL-1 or the Epidermal growth factor receptor (EGFR) siRNA. IL-6 levels were quantified in cell culture medium 24 h after induction with poly(I:C). C) Effect of truncated peptides in poly(I:C) mediated IL-6 production in the presence of LL-37. The effects of the peptides were determined in BEAS-2B cells knocked down for either a nonspecific control or for FPRL-1.
Figure 7:
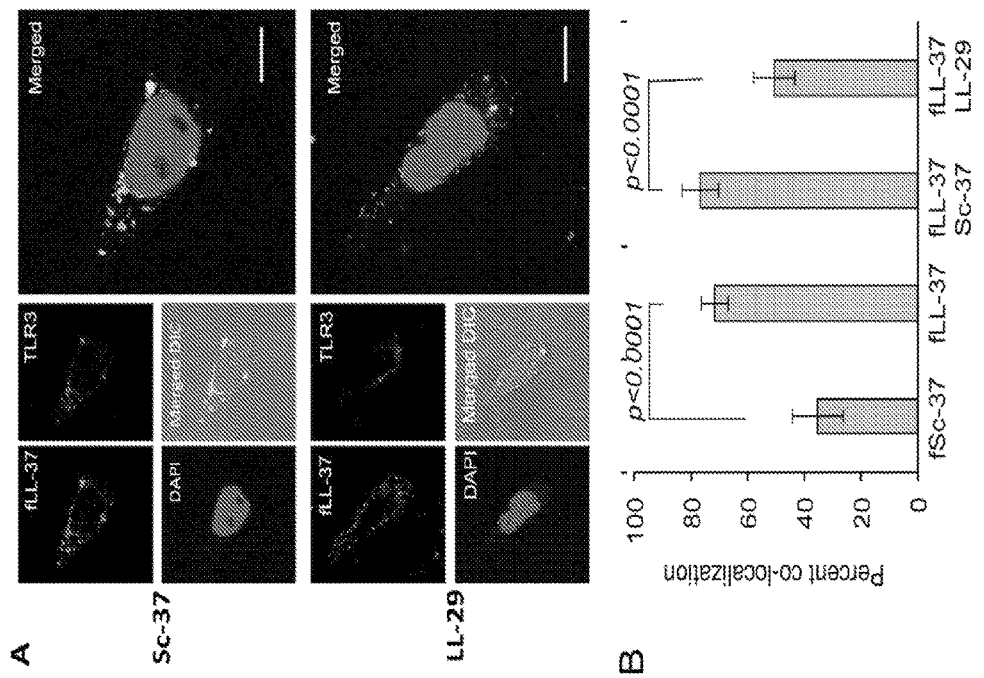
FIG. 7. LL-29 can decrease the co-localization of fLL-37 and TLR3 in BEAS-2B cells. A) Fluorescent micrographs of the locations of LL-29 or Sc-37 added to cells along with LL-37 and poly(I:C). LL-37 was added to a final concentration of 1.0 µM and poly(I:C) to a final concentration of 130 ng/ml. TLR3 was detected with goat anti-TLR3 antibody and a Alexa-488-labeled anti-goat secondary antibody. B) Quantification of the percent co-localization of LL-37 and TLR3. fSc-37 was used as a control. Quantitative co-localization data are the mean values for 20 cells assessed from three independently prepared samples. The p values were calculated by using the Student t-test.

Interpretation of LL-37 interaction with the FPRL-1 is more complicated. FPRL-1 is required to traffic the complex of LL-37 and dsRNA to endosomes. Therefore, LL-37 derivatives that are defective for dsRNA binding will be defective for endocytosis through the FPRL-1 receptor. Interestingly, cells treated with LL-29 along with LL-37 and poly(I:C) were reduced for the enhancement of dsRNA signaling from the FPRL-1 receptor (FIG. 6). Furthermore, LL-37 was decreased in co-localization with TLR3 in endosomes (FIG. 7). Given that LL-29 can interact with LL-37, it is likely that a heterocomplex of LL-37 and LL-29 is unable to traffic dsRNA using the FPRL-1 receptor. The decrease in dsRNA concentration in endosomes likely reduces signal transduction by TLR3.

TLR3 signaling must be tightly regulated to allow proper response to pathogen infection while limiting the response to self-molecules. LL-37 likely plays an important role in both responses by enhancing TLR3 recognition of viral dsRNA. It is also known to trigger inflammatory response to self-DNA by TLR9. The ability of LL-29 to antagonize the activity of LL-37 could be developed to reduce elevated immune responses associated with high levels of LL-37 and self-nucleic acid. Truncated parathyroid peptides have been developed to promote bone morphogenesis with reduced ability to promote bone resorption. Notably, LL-29 retains the ability to suppress TLR4 signaling (Table 1). It is possible that antagonists of LL-37 can remain competent as antimicrobial peptides that suppress the inflammatory response associated with bacterial infections. One non-limiting theory is that antagonists of LL-37 remained LL-37's ability to sequester TLR4 receptor's ligand such as LPS, preventing TLR4 signaling triggered by LPS.

Interestingly, we identified the antimicrobial peptides from other mammals and identified that several can suppress the LPS induced inflammatory response without activating the nucleic acid-induced inflammatory response. Singh et al. (2012) had previously reported that the LL-37 ortholog from mouse, mCRAMP failed to activate cytokine production induced by TLR3 in both human and mouse cell lines. Herein, we analyzed the LL-37 orthologs from Rhesus monkeys, pig, sheep, guinea pigs, rabbit, as well as mouse (FIG. 14A). All peptides were chemically synthesized and assayed for the induction of inflammatory cytokine IL-6 in the presence of the double-stranded RNA mimic, poly(I:C) or the Reovirus dsRNA, Reo S4 (FIGS. 14B and 14C). As expected, mCRAMP was unable to enhance IL-6 production with either poly(I:C) or Reo S4. However, the peptides from pig (PAMP-37), sheep (SMAP-20), and rabbits (CAP-11) all failed to enhance signaling by poly(I:C) and Reo S4. The three peptides also failed to induce signaling by the ssDNA ligand for the Toll-like receptor 9, ODN2009 (FIG. 14D). Importantly, all LL-37 orthologs tested had the ability to reduce IL-6 production in response to LPS (FIG. 14E). Notably, the monkey and the guinea pig LL-37 ortholog, RL-37, had activities that are more similar to that of the human LL-37 (FIG. 14 B-E).

LL-37 engages the Formyl peptide receptor-like 1 (FPRL-1) receptor to deliver nucleic acids into endosomes, where activation of the Toll receptors that recognize nucleic acids takes place (Singh et al., 2014). We sought to determine whether the LL-37 orthologs from other mammals could also use the FPRL-1 in the human BEAS-2B cells to deliver dsRNA. BEAS-2B cells were treated with poly(I:C) along with the peptides from pig, sheep, rabbit, and mouse had reduced ability to use the FPRL-1 to activate IL-6 production. Interestingly, the monkey and guinea pig peptides had activities more similar to the human LL-37 in the use of the FPRL-1 receptor for activation of IL-6 production.

As will be exemplified in the examples below, we sought to examine the antimicrobial activities of LL-37 and LL-29 and their orthologs in other mammals. The CLSI M110-S25 assay was used to examine the inhibition of the bgrowth of *Escherichia coli* ATCC 25922 and to calculate the minimal inhibitory concentration (MIC). Bacterial cultures were infused with LL-37 or LL-29 along with antibiotics, doxorubicin, kanamycin, and trimethylprim to enable analysis of the synergistic effects of LL-37 and LL-29 with the antibiotics. LL-37 additively improved the MIC by 2-fold. Importantly, LL-29 improved the MIC by was at least 4-fold with all three antibiotics.

Thus, LL-29, which has reduced activation of nucleic acids induced innate immune responses, can suppress the activity of LL-37 yet it retains the effective killing of the bacterium *E. coli* and can suppress the inflammatory response from bacterial lipopolysaccharides. The robust synergetic antimicrobial effect of LL-29 compared to LL-37 is shown in Table 2 of Example 11.

Materials and Methods

Cells and Reagents—

The BEAS-2B cell line was from the American Type Culture Collection and cultured in BEGM media with its supplements (11; Lonza). Proteasome inhibitors MG132 and Lactacystin (Calbiochem) were dissolved in ethanol and dimethyl sulfoxide (DMSO), respectively. Cathepsin inhibitor z-FA-FMK (Santa Cruz Biotechnology) was dissolved in DMSO. Endosome acidification inhibitors ammonium chloride, chloroquine, and Bafilomycin A1 (Sigma-Aldrich) were dissolved in water or DMSO. Poly(I:C) and lipopolysaccharide (LPS) were from Invivogen. Reovirus (RV) dsRNA S4 was prepared by in vitro transcription as described in Lai et al. (11). Peptides without or with covalently attached fluorophores were custom synthesized by AnaSpec Inc. and purified to greater than 95% purity. Antibody to detect LL-37 was from Santa Cruz Biotechnology (Cat # Sc-166770). siRNAs were from Santa Cruz Biotechnology and specific to FPRL1 (sc-40123), EGFR (sc-29301), or a nonspecific control siRNA (sc-37007).

Fluorescence Polarization Assay—

Peptide binding to poly(I:C) was analyzed by monitoring fluorescence polarization using the Synergy H1 microplate reader (BioTek). Fluorescein-labeled LL-37 was titrated to a 100 µL solution containing poly(I:C) and phosphate buffers at different pHs. Interactions between LL-37 and other peptides were analyzed using LL-37 labeled at the N-terminus with fluorescein (0.1 µM), and peptides were titrated from 1 nM to 1000 nM in phosphate buffer at pH 7.0. Interaction between poly(I:C) and different peptides was determined by titrating fluorescein-labeled poly(I:C) (0.1 µM) with peptides added to final concentrations of 10 to 500 nM in phosphate buffer at pH 7.4. All polarization assays were performed in triplicate.

Dynamic Light Scatter Spectroscopy—

The hydrodynamic radii of LL-37 and other peptides were monitored by a Zetasizer Nano-S instrument (Malvern Instruments). All measurements were taken with 1 µM of peptide dissolved in phosphate buffer adjusted to the desired pH at 22° C.

Quantification of IL-6—

IL-6 production was quantified by ELISA using the OptEIA™ kit (BD Biosciences). A typical assay used $2\times10^4$ BEAS-2B cells/well grown for 24 h in flat bottom 96-well plates. Poly(I:C) was added to a final concentration of 0.13 µg/ml. Antimicrobial peptides were added to the cell culture medium to a final concentration of 3 µM unless specified otherwise. All ELISA results shown were performed in triplicate and in at least three independent experiments.

RNA Silencing Assays—

BEAS-2B cells were seeded at $2\times10^6$ cells per 6-well plate for 6 h prior to transfection with 30 nM of a pool of three siRNAs from Santa Cruz Biotechnology. Transfections were done using Lipofectamine 2000.

Cells were grown on poly-L-lysine (Life Technologies). The level of target mRNA was analyzed using qRT-PCR and normalized to the levels of GAPDH mRNA. The sequences of the primers will be made available upon request. Poly(I:C) was added 48 h after siRNA transfection and IL-6 levels in the culture media were collected 24 h later.

Confocal Microscopy—

Cells were grown on poly-L-lysine coated coverslips to 60% confluency. After 1 h incubation with fluorescently-labeled peptides in the absence or presence of poly(I:C), the cells were washed with PBS and fixed with 4% paraformaldehyde for 15 min at room temperature. The cells were again washed with PBS and mounted on glass slides with anti-fade mounting medium and DAPI (Life Technology), then dried overnight in the dark. Micrographs were acquired with a Leica TCS SP5 confocal inverted-base microscope with a 63× oil objective. Images were analyzed by Leica LAS AF and Image J software. Colocalization of fluorophores was quantified using the Image J plug-in tool JACoP (16).

Förster Resonance Energy Transfer (FRET) Assays—

LL-37 and poly(I:C)'s ability to interact within cells was analyzed by monitoring their ability to transfer energy, as measured by FRET assays (17). Fluorescein-labeled LL-37 and rhodamine-labeled poly(I:C) were added to the medium of cells in the absence or presence of inhibitors of endosome acidification and incubated for 1 h. The cells were then washed with PBS, fixed with 4% paraformaldehyde for 15 min at room temperature, then processed for microscopy as reported previously (18). Fluorescein was excited with a 488 nm laser and emission was monitored by a Leica TCS SP5 confocal inverted-base microscope with a 63× oil objective. Data analysis used the Leica LAS AF software.

Statistical Analysis—

All data shown are the means and ranges for one standard error for a minimal of three independent samples. Data sets were compared using the Student t-test calculated with GraphPad Prism 5 software.

Reversible Crosslinking, Peptide Fingerprinting—

LL37 was incubated with poly(I:C) at the molar ratios indicated, then crosslinked with the addition of 0.1% formaldehyde. After 15 min., formaldehyde was quenched by the addition of 2 M glycine, and LL37 was digested with 1:20 (w/w) ratio of trypsin overnight. Poly(I:C) was selectively precipitated with lithium chloride along with the covalently crosslinked peptides from LL37 as previously described (19). Protein-RNA crosslinks were reversed by heating the sample for 1 h at 72° C., and eluted peptides were analyzed using a Bruker Autoflex II MALDI-TOF mass spectrometer (Agilent Technologies).

MIC assays were performed according to protocols for broth microdilution according to the Clinical Laboratory Standards Institute (CLSI, 2015. Methods for Dilution Antimicrobial susceptibility tests for bacterial that grow aerobically; Approved standard—tenth edition).

EXAMPLES

It should be understood that the foregoing relates to exemplary embodiments of the disclosure and that modifications may be made without departing from the spirit and scope of the invention as set forth in the following claims.

Example 1. LL-37 Binding to Ligands In Vitro is Dependent on pH

In this example we establish that LL-37 binding to ligands in vitro are pH dependent. This is significant because varying pH environments may result LL37's binding affinity, thus alter the LL-37 associated signaling molecules' binding status.

LL-37 accompanies dsRNA to endosomes containing TLR3. However, it is unknown whether LL-37 will release the dsRNA in endosomes. Johansson et al. (1998) have previously determined that a neutral pH is required for the activity of LL-37. We seek to determine whether LL-37 binding to dsRNA can be affected by pH. A fluorescent polarization assay was performed with fLL-37, which has a 5' carboxyfluorescein coupled to the N-terminus of LL-37 (FIG. 1A). fLL-37 was previously demonstrated to enhance TLR3 signaling by dsRNA and to suppress TLR4 signaling by LPS. In a pH 7.4 phosphate buffer, fLL-37 polarization increased as a function of poly(I:C) concentration, indicating an interaction between the two molecules (FIG. 1B). LL37 binding to poly(I:C) significantly decreased when the pH of the buffer was decreased. A fluorescently-labeled peptide that had a randomized order of the amino acids present in LL-37, fSc37, did not interact with poly(I:C) titrated into the solution at any of the pHs tested (FIG. 1C). These results suggest that LL-37 binds to poly(I:C) in a pH and sequence-dependent manner.

We determined whether fLL-37 binding to heteropolymeric dsRNA was dependent on the solution pH. LL-37 binding to Reovirus S4 dsRNA was better at pH 7.4 than at pH 6.4 (FIG. 1D). Other polyanionic molecules, including LPS and the sense-strand of the S4 RNA were also preferentially bound by fLL-37 at neutral pHs (FIG. 1D).

These results show that LL-37 binds anionic polymers in a pH-dependent manner in vitro. For the remainder of this study, we will use poly(I:C) as a dsRNA ligand for LL-37.

Example 2. Acidification Accompanies Release of Poly(I:C) from the LL-37/Poly(I:C) Complex in BEAS-2B Cells In this example we establish that LL37 bound double-stranded nucleic acids are released in acidic environment where they can enhance TLR3 mediated proinflammatory responses, presumably by increasing the available double strand nucleotides to trigger TLR3 proinflammatory signaling pathways.

Figure 2:
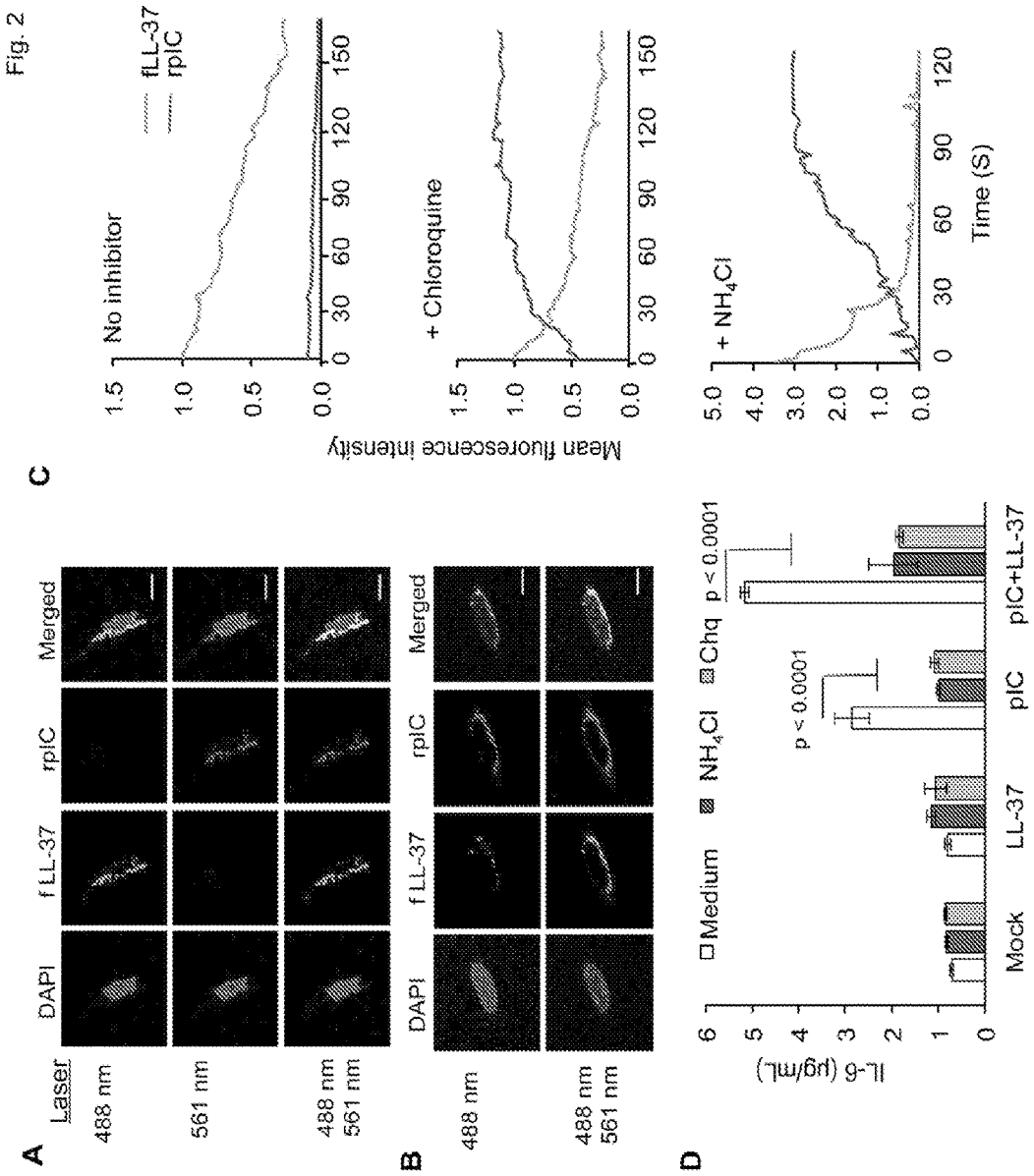
FIG. 2. LL-37 and poly(I:C) interaction in BEAS-2B cells is affected by endosome acidification. A) Micrographs of the intracellular locations of fLL-37 and rpIC 60 min after their addition to lung epithelial BEAS-2B cells. fLL-37 is the second column and rpIC is in the third column. Co-localization of the two fluorescent peptides is shown in the fourth column. Note that the signal for rhodamine was not observed with excitation at 488 nm (third panel from the left, upper row) due to the lack of Förster resonance energy transfer from fluorescein to rhodamine. B) Micrographs of the intracellular locations of fLL-37 and rpIC in BEAS-2B cells. The cells were treated with fLL-37 and rpIC for 60 min and pretreated with the endosome acidification inhibitor chloroquine or ammonium chloride. Excitation of fluorescein was at 488 nm and excitation of rhodamine was at 561 nm. Note that when fluorescein was excited with 488 nm, cells also emitted fluorescence consistent with that of rhodamine (third panel from the left, top row), indicating that FRET occurred between fLL-37 and rpIC. C) Real-time monitoring of the fluorescence of the fLL-37 and rpIC in BEAS-2B cells treated or not treated with endosome inhibitors. All three panels contain cells excited to activate fluorescein with only 488 nm laser and detecting fluorescence for both fluorescein and rhodamine. Upper panel: BEAS-2B cells treated with both fLL-37 and rpIC, but not with endosome acidification inhibitors did not exhibit rhodamine fluorescence. Middle panel: BEAS-2B cells treated with both fLL-37 and rpIC, and the endosome acidification inhibitor choroquine exhibited resonance energy transfer from fLL-37 to rpIC. Bottom panel: BEAS-2B cells treated with both fLL-37 and rpIC, and the endosome acidification inhibitor ammonium chloride exhibited FRET. D) Enzyme-linked immunosorbent assay (ELISA) detection of IL-6 in the presence of endosomal acidification inhibitor, poly(I:C) and poly(I:C)/LL-37. All data points contain the mean of experiments performed in triplicate and p values were calculated by using the Student t-test.

It is established that LL-37 bound dsRNA traffics into endosomes to enhance TLR3 activity. We sought to determine whether the LL-37/poly(I:C) complex will dissociate in acidified endosomes of BEAS-2B cells, a human lung epithelial cell line that expresses endogenous FPRL-1, a receptor for the LL-37/dsRNA complex and TLR. Rhodamine-labeled poly(I:C) (rpIC) and fLL37 form a FRET pair and rpIC was previously shown to activate TLR3 signaling. Both fLL-37 and rpIC localized to endosomes (FIG. 2A). However, excitation of the fluorescein-labeled LL-37 did not result in energy transfer and fluorescence of the rhodamine on rpIC (FIGS. 2A and 2C). This result suggests that LL-37 and poly(I:C) were no longer in physical contact in endosomes. However, cells treated with either chloroquine or ammonium chloride to inhibit endosome acidification prior to the addition of fLL-37 and rpIC exhibited Forster resonance energy transfer (FIGS. 2B and 2C). These results suggest that endosome acidification is associated with the dissociation of the LL-37/poly(I:C) complex in cells. Inhibition of endosome acidification also inhibited IL-6 production, which is consistent with signaling by TLR3 requiring acidified endosomes (FIG. 2D).

Example 3. LL-37 Oligomerization In Vitro is Affected by pH

In this example, we establish that LL-37 oligomerization is affected by pH. This is significant because potential interactions of LL-37 antagonists with native LL-37 may affect the effects of antagonists.

Figure 3:
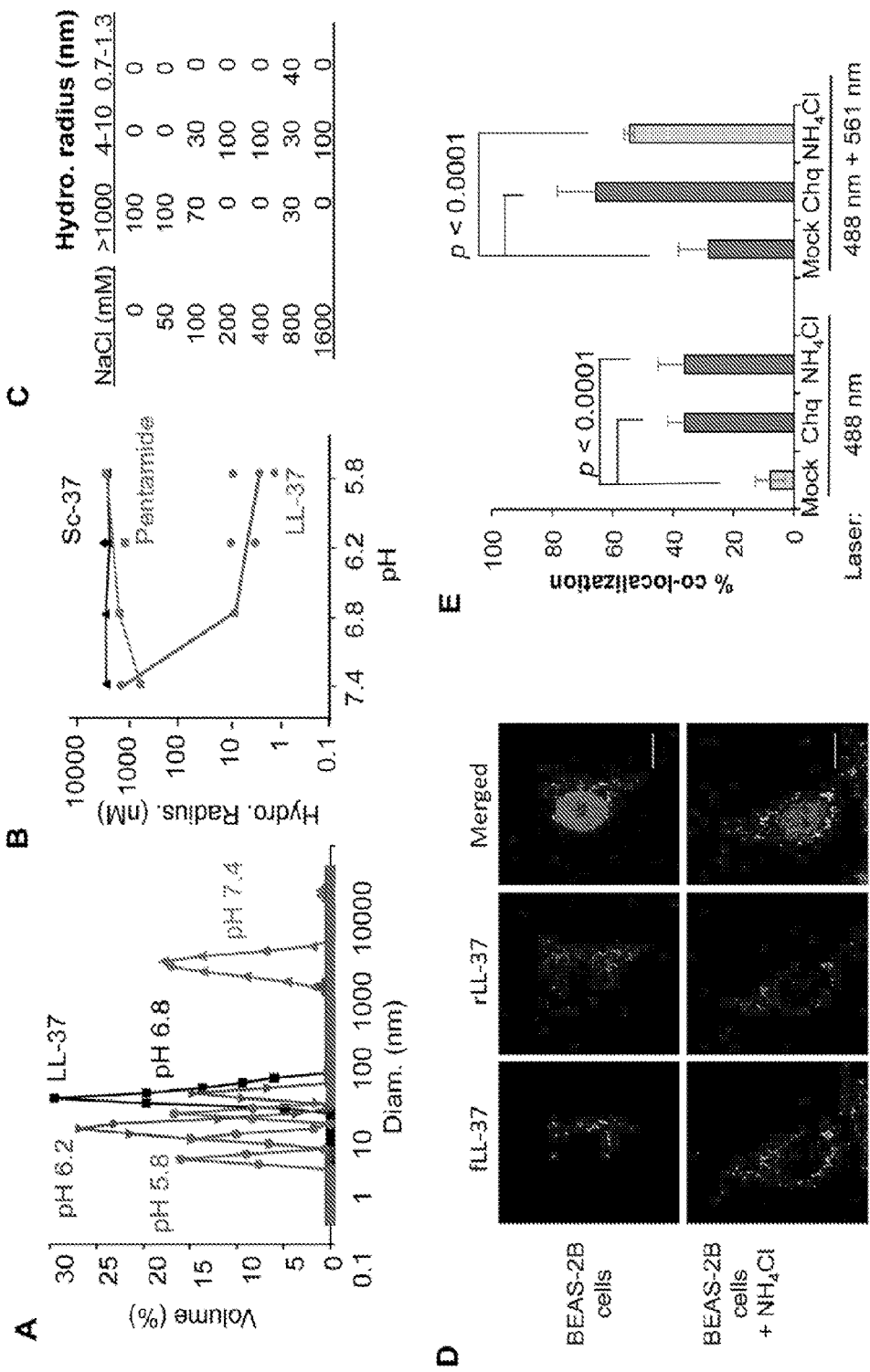
FIG. 3. Oligomerization of LL-37 depends upon pH. A) LL-37 forms particles that are micrometers in hydrodynamic radii at neutral pH and the particles dissociate when the pH is decreased. All assays were performed with LL-37 at a concentration of 1 µM in phosphate buffer. B) Peptides Sc-37 and Pentamide form particles that do not dissociate in acidic buffer. C) LL-37 particles will dissociate in the presence of salt. The hydrodynamic radius of ~1 µM LL-37 was determined in a pH 7.4 phosphate buffer adjusted to contain the concentration of NaCl indicated. D) fLL37 and rLL-37 colocalize in endosomes of BEAS-2B cells. fLL-37, rLL-37, and poly(I:C) were added to BEAS-2B cells that were either mock-treated or treated with ammonium chloride and imaged 60 min later by excitation at 488 nm or at 561 nm. The micrograph images were then merged to show the co-localization of the two fluorescent peptides. E) Co-localization of fLL-37 and rLL-37 in BEAS-2B cells was quantified in the absence or presence of endosomal acidification inhibitors. To detect both peptides, the cells were excited with 488 and 561 nm laser. To determine FRET between the two peptides, the cells were excited at only 488 nm laser, which activates fluorescence of fLL-37 and the emissions for both fluorescein and rhodamine were determined. The data shown were quantified from 20 independent cells from three independently prepared samples. The p values were calculated by using the Student t-test.

LL-37 forms higher order oligomeric complexes. We used dynamic light scatter spectroscopy to determine whether pH will affect the oligomerization state of LL-37 in solution. At pH 7.4, the average hydrodynamic radius of LL-37 was ~1 µm. However, a decrease in the buffer pH resulted in LL-37 dissociating to less than 10 nm (FIG. 3A). Sc-37 also formed a higher order complex of ~1 µm in radius, but this complex was not affected by acidification of the buffer (FIG. 3B). Pentamide, which had the five acidic residues in LL-37 replaced with neutral-polar residues, also failed to dissociate from a higher order complex as a function of pH.

The results with Pentamide suggest that ionic interactions between the LL-37 peptides contribute to the formation of LL-37 oligomers. To address this, we examined whether salt concentrations will affect the hydrodynamic radii of LL-37. The reactions were performed in a pH 7.4 buffer. In solutions with up to 50 mM NaCl, LL-37 was in complexes with hydrodynamic radii of >1 µm. At ca. 100 mM NaCl, smaller complexes of 4-10 nm were observed (FIG. 3C). With NaCl of 200 mM or higher, LL-37 only had a hydrodynamic radii of 2-5 nM. The sensitivity of higher-order complexes of LL-37 to salt is consistent with ionic interactions being responsible for the association between LL-37 subunits.

Example 4. LL-37 Oligomerization in Cells is Affected by pH

In this example we further establish that LL-37 oligomerization in cells is also affected by pH. This further proves the significance of LL-37 (whether native homologous or antagonist heterologous complex is sensitive to microenvironment and provides insights on how to manipulate the complex to better utilize different activities of LL37 complex.

To examine whether LL-37 forms higher order oligomers in cells, we used a 1:1 mixture of fLL-37 and rhodamine-labeled LL-37 (rLL-37). When the two peptides were added to the medium of BEAS-2B cells, they co-localized to endosomes within 30 minutes (FIG. 3D). However, relatively little FRET was observed unless cells were treated with ammonium chloride or chloroquine to inhibit endosome acidification (FIGS. 3D and 3E). Identical results were observed when the cells were treated with a 1:1 mixture of fLL-37 and rLL-37 which was added along with poly(I:C) (data not shown). These results suggest that the LL-37/poly (I:C) complex dissociates upon endosome acidification.

Example 5. Endosome Acidification is Associated with LL-37 Turnover

In this example we monitored LL37 complex upon the release of double-stranded nucleic acid molecules.

Acidification of endosomes can activate cathepsins that can cleave TLR3, 7, and 9 and increase signaling. We examined whether LL-37 would be subject to proteolysis, possibly by cathepsins. BEAS-2B cells were treated with LL-37 in the absence or presence of poly(I:C) for 15 min, then washed with phosphate-buffered saline and incubated with fresh medium. The cells were harvested over time, lysed and subjected to Western blot analysis. LL-37 accumulation decreased over time, with an estimated half-life of 1 h (FIG. 4A, 4B). Cells treated with ammonium chloride or the cathepsin inhibitor Z-FA-FMK had half-lives in excess of 12 h (FIG. 4A, 4B). These results suggest that when LL-37 releases dsRNA upon endosome acidification, it is subject to proteolysis.

Example 6. Residues in LL-37 that Contact Poly(I:C)

In this example we seek to determine how residues in LL-37 contact poly(I:C) using a reversible crosslinking-peptide fingerprinting method (RCAP).

RCAP has been used to map the RNA-contacting regions within several protein-RNA complexes using formaldehyde, a bifunctional crosslinking agent that crosslinks primary amines that are within 2 angstroms of each other.

Figure 10:
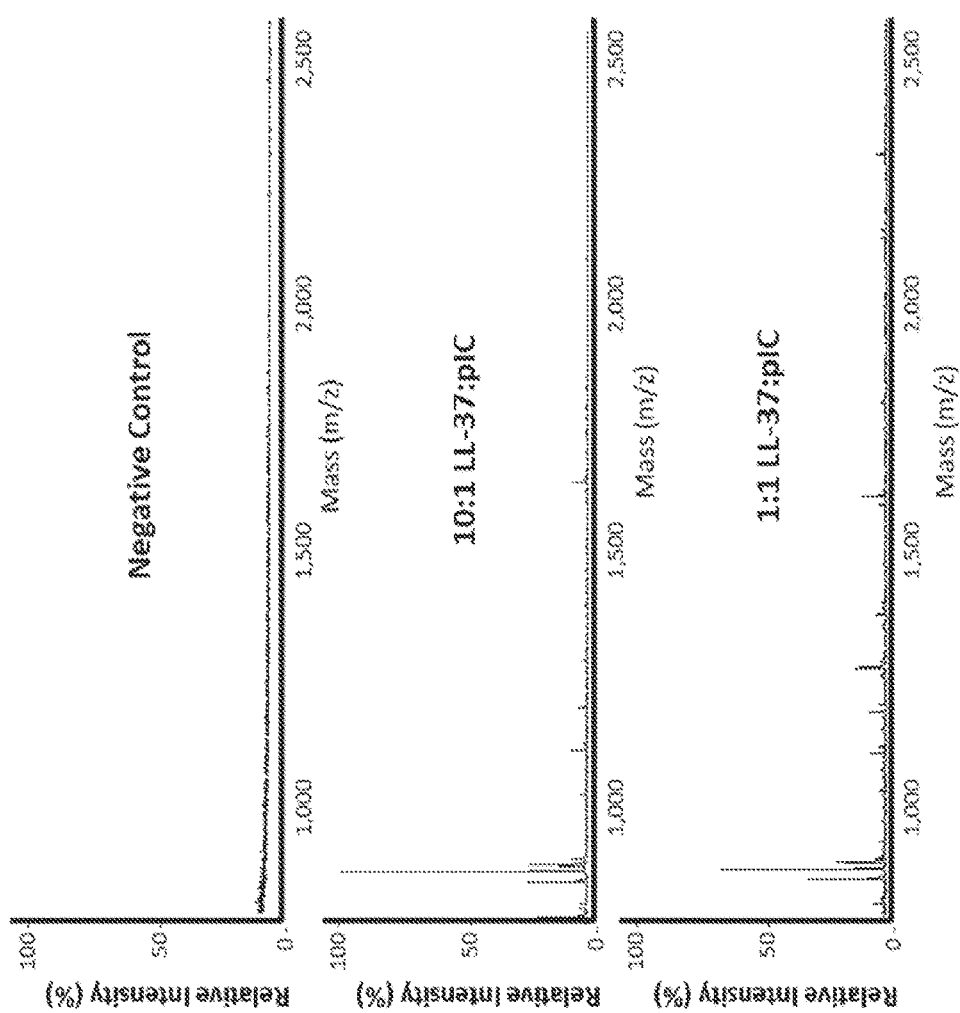
FIG. 10. Sample mass spectra from the RCAP assay detecting peptide fragments from LL-37 crosslinked to poly(I:C). The negative control was performed with an assay containing all of the components, but not treated with formaldehyde. The samples containing LL-37 and poly(I:C) were processed for RCAP analysis and the results shown in FIG. 5 of the Singh et al. manuscript. Only the samples where LL-37 and poly(I:C) were present and processed had detectable peptides.

Crosslinked LL-37/poly(I:C) were exhaustively digested with trypsin to cleave C-terminal to lysines and arginines (FIG. 5A). Poly(I:C) and peptide fragments crosslinked to poly(I:C) were selectively precipitated with LiCl. The crosslinked peptides co-purified with poly(I:C) were reversed and subjected to mass spectrometric analysis. Control reactions performed without formaldehyde did not identify peptides from LL-37 (FIG. 10). Several peptides derived from LL-37 were observed with LL-37/poly(I:C) at both a 1:1 molar ratio and at a 10:1 mass ratio. All peptides matched to within 0.5 Daltons of the expected LL-37 tryptic fragments (FIG. 5B). Both the N- and C-terminal portions of LL-37 were found to be in contact with poly(I:C) (FIG. 5C). Overlapping peptides were observed, suggesting that some lysine and arginine residues were only partially crosslinked to poly(I:C), since some sites remained accessible to trypsin cleavage (FIGS. 5B and 5C).

Example 7. Mapping Regions in LL-37 Required for Function

In this example we establish LL-37's key regions required for its various functions. With this knowledge it is possible to design LL-37 antagonists that are fit for enhancing or inhibiting a certain function of native LL-37.

To better define how residues in LL-37 contribute to function, several variants derived from LL-37 were tested for: 1) repression of TLR4 signaling by LPS, 2) enhancement of TLR3 signaling by poly(I:C), and 3) binding to LL-37. Signaling by TLR3 and TLR4 were monitored using ELISA to detect IL-6 secreted into the medium of BEAS-2B cells.

N- and C-terminal truncations in LL-37 retained the ability to suppress TLR4 signaling (Table 1). Pentamide, which had all acidic residues in LL-37 replaced with neutral-polar residues, was the only one that failed to suppress TLR4 signaling. These results suggest that multiple regions of LL-37 can interact with LPS to suppress TLR4 signaling.

In contrast, all LL-37 truncations negatively affected TLR3 signaling. Three peptides, LL9-29, Pentamide, and mCRAMP, failed to enhance TLR3 signaling. Removal of the N-terminal 8-residues, the C-terminal 8-residues of LL-37, or the replacement of the C-terminal 4 residues with those from mCRAMP resulted in peptides that retained partial activity for enhancing TLR3 signaling. These results suggest that both terminal regions of LL-37 are required for wild-type level of interaction with poly(I:C) to activate TLR3 signaling (FIG. 5, Table 1).

Figure 9:
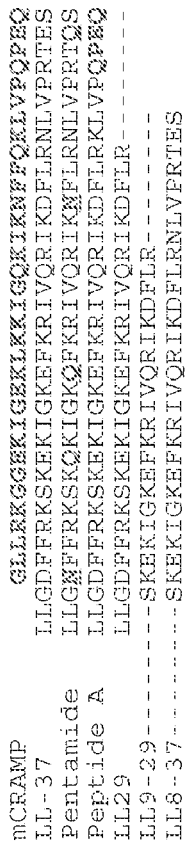
FIG. 9. Dissociation of LL-37 and derivatives as a function of pH. The upper panel shows the amino acid sequence of the peptides. The bottom one shows the average hydrodynamic diameters of the particles as a function of pH. The names for the peptides used are color-coded to match the line graphs. All peptides were assayed at 1 mM concentration in phosphate buffer adjusted to the stated pH. Of the peptides, only LL-29 and LL-37 dissociated as a function of pH.
Figure 9:
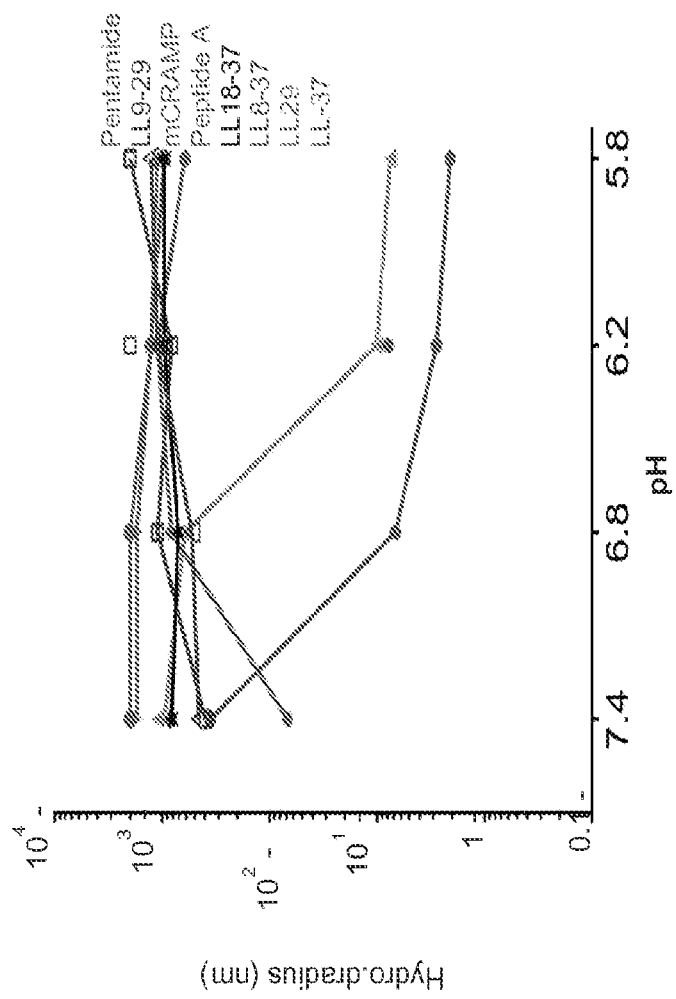

We tested whether the LL-37 variants dissociate in a pH-dependent manner using dynamic light scatter spectroscopy. LL-29, which lacks the C-terminal 8 residues of LL-37, readily dissociated into nanometer-sized particles (Table 1, FIG. 9). Peptide A, with only the C-terminal four residues of LL-37 replaced with mCRAMP residues, was also reduced for the ability to dissociate under acidic pH conditions (FIG. 9). Therefore, while the terminal 8 residues are not required for oligomer dissociation, residues from LL-37 are needed for proper peptide-peptide interaction. Peptide LL9-29 that lacked both the C- and N-terminal regions, also failed to dissociate (Table 1).

Figure 11:
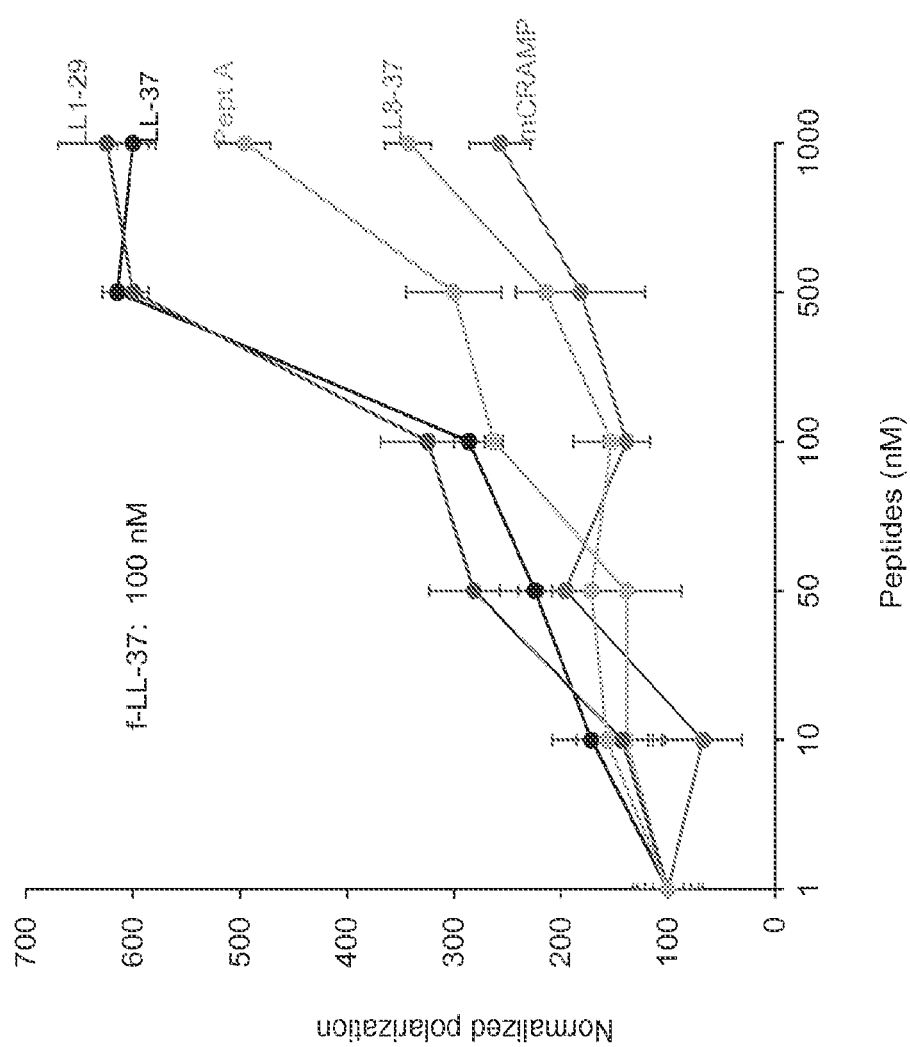
FIG. 11. Results from fluorescence polarization assay examining the interaction between peptides and fLL-37. An increased polarization value of fLL-37 indicates interaction of the peptides. Of the peptides tested, LL-29 and LL-37 have comparable ability to interact with fLL-37. Peptide A and LL8-37 retain partial activity to interact with fLL-37.

Since LL-29 retains the ability to change its oligomerization state in a pH-dependent manner, we examined whether it can bind WT LL-37. In a fluorescence polarization assay, LL-29 interacted with fLL-37 to the same degree as LL-37 (Table 1, FIG. 11). Peptide A retained partial interaction with fLL-37 in this assay while LL9-29, which lacks the N-terminal 8 residues of LL-37, did not (Table 1). The N-terminal 29-residues of LL-37 are thus capable of intermolecular interaction with LL-37.

Example 8. LL-29 can Inhibit LL-37-Enhanced TLR3 Signal Transduction

In this example we tested our peptide antagonists' effect on native LL-37 functions.

Figure 12:
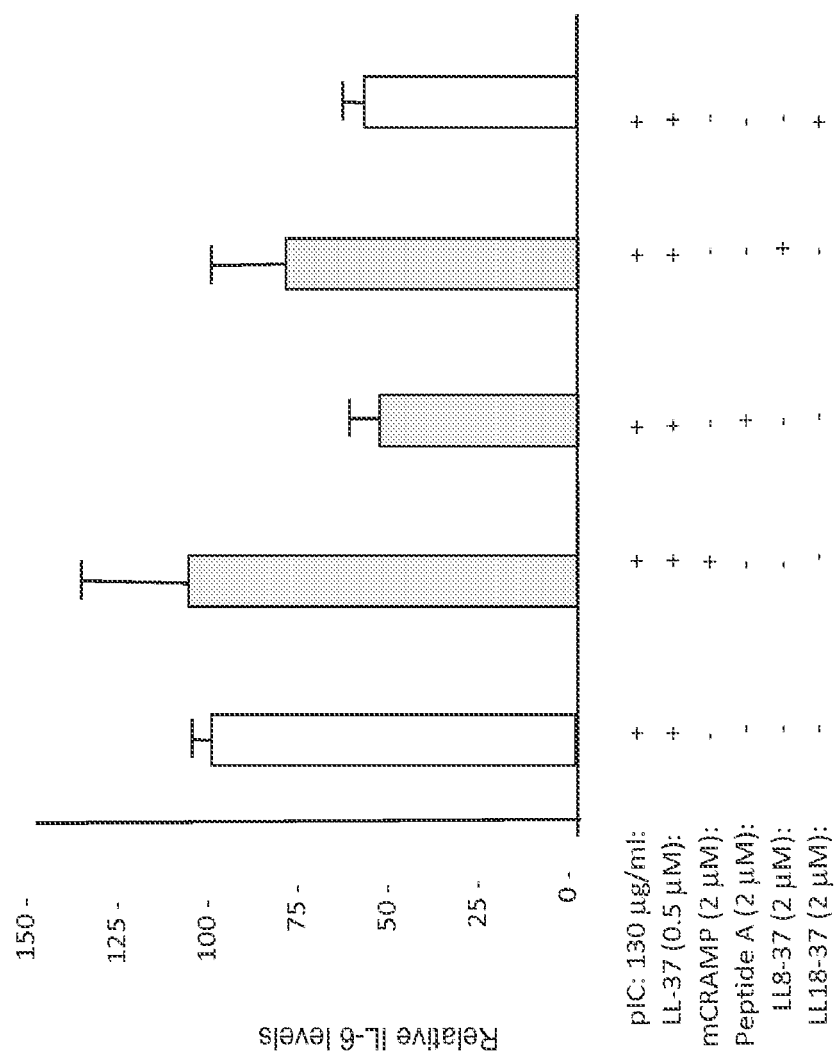
FIG. 12. Examination of peptides for the ability to antagonize LL-37 activity in enhancing TLR3 signaling in BEAS-2B cells. TLR3 signaling was assessed by the amount of IL-6 secreted into the medium. Peptide A and possibly peptide LL18-37 can partially antagonize the enhancement of TLR3 signaling.

We examined whether LL-29 could affect the enhancement of TLR3 signaling by WT LL-37/poly(I:C). An increasing amount of LL-29 along with a constant amount of LL-37/poly(I:C) was used to assess IL-6 production in BEAS-2B cells. The presence of LL-29 reduced the enhancement of TLR3 signaling by LL-37 in a concentration-dependent manner (FIG. 6A). At a four molar excess of LL-29 relative to LL-37, IL-6 production was comparable to the level observed in the absence of LL-37 (FIG. 6A). That is, LL-29 abrogated LL-37's ability to enhance TLR3 signaling. That is, LL-29 is an example of a peptide antagonist of LL-37 function. Peptide A could also antagonize LL-37's enhancement of TLR3 signaling, but to a lesser degree than LL-29 (FIG. 12).

Interestingly, LL-29 added along with LL-37 to BEAS-2B cells retained the ability to suppress TLR4 signaling in response to LPS (FIG. 6A). A two molar excess of LL-29 relative to LL-37 did not reduce TLR4 signaling (FIG. 6A). At a four molar excess of LL-29 to LL-37, IL-6 production in response to LPS was still at 64% of the control level without either of the two peptides. These results suggest that LL-29 can preferentially antagonize LL-37's enhancement of TLR3 signaling while retaining the ability to suppress TLR4 signaling.

Thus LL-29 can inhibit TLR3 signaling, which predominantly leads to proinflammatory cytokine production and links to autoimmune diseases. At the same time, LL-29 retains the suppression of TLR4 signaling with LPS (to contain unwanted inflammation). These features make LL-29 and its derivatives ideal for drug development toward autoimmune diseases regulated by TLR3 and TLR4 signaling pathways. It is understood that any similar LL-29 derivatives presenting such functions toward native LL-37 are included in the scope of this application's protection.

Example 9. LL-29 can Prevent LL-37/Poly(I:C) Trafficking Using the FPRL-1 Receptor In this example we establish non-limiting mechanisms for peptide antagonists LL-29, or Peptide A acting on LL-37. It is possible that the peptide antagonists abrogate native LL-37 interaction with FPRL-1 receptor. It is also possible that the peptide antagonists deplete native LL-37 so that FPRL-1 receptor becomes irrelevant for the dsRNA trafficking to endosome.

Figure 13:
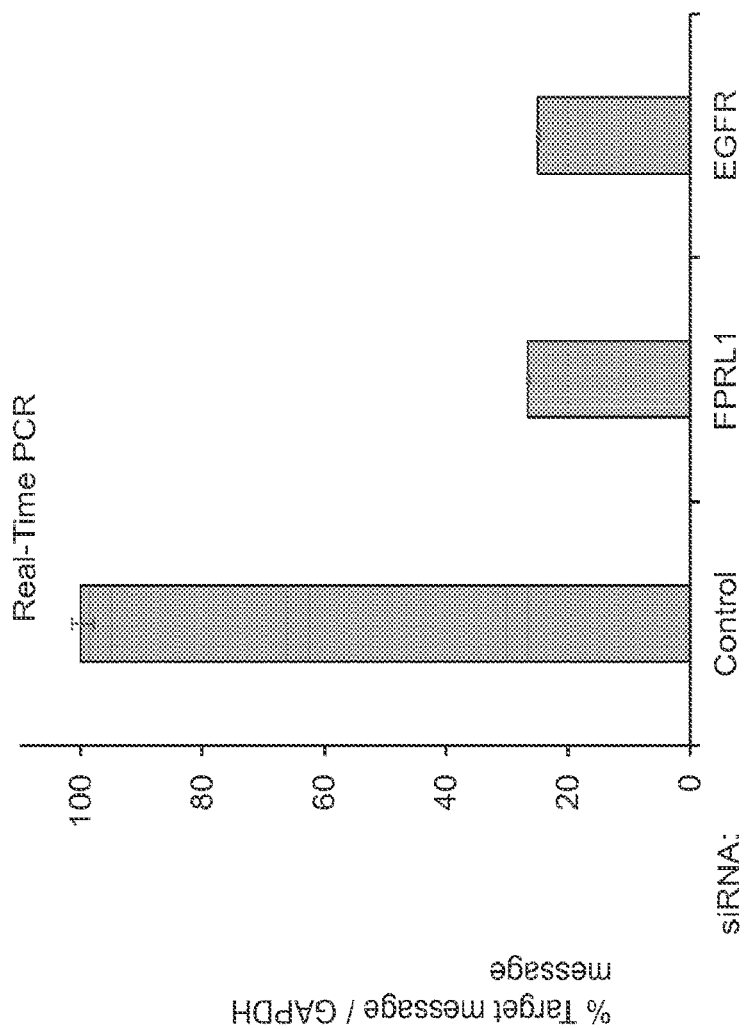
FIG. 13. Quantification of the knockdown of FPRL-1 and EGFR messenger RNAs by siRNA. SiRNA treatment knocked down the FPRL-1 and EGFR message to less than 30% of a control. BEAS-2B cells treated for 48 h with transfected siRNA were lysed and the total RNA used for quantitative reverse transcription and PCR. The amount of FPRL-1 and EGFR cDNA were normalized with the GAPDH cDNA from the same sample. In the sample treated with a nonspecific control siRNA, the amount of FPRL-1 cDNA was quantified.

LL-37's enhancement of TLR3 signaling required trafficking of LL-37/poly(:C) to endosomes via the FPRL-1 receptor. Therefore, we examined whether LL-29 used the FPRL-1 receptor to enter cells. siRNA was used to knock down the expression of either FPRL-1, EGFR, or TLR3. Quantitative RT-PCR analysis showed that the FPRL-1 message was reduced to approximately 20% of the control siRNA-treated samples (FIG. 13). Co-localization of fLL-37 and rpIC was reduced to less than a third of the control. Cells knocked down for TLR3 expression had reduced IL-6 production in response to poly(I:C) both in the absence and presence of LL-37, demonstrating that IL-6 production requires TLR3 (FIG. 6B). Knockdowns performed with siRNAs to either a nonspecific control or EGFR had no effect on the enhancement of IL-6 production. Pentamide, LL8-37, or LL-29 added to cells along with poly(I:C) also did not enhance IL-6 production with knockdown of either FPRL-1 or EGFR (FIG. 6B). These results suggest that truncations of LL-37 or changes in subunit interactions in LL-37 derivatives will affect engagement of the FPRL-1 receptor.

Will LL-29 affect the use of the FPRL-1 receptor by the LL-37/poly(I:C) complex? BEAS-2B cells knocked down for FPRL-1 were treated with LL-37 along with additional concentrations of LL-37, Pentamide, LL-29, Peptide A, or LL8-37 (FIG. 6C). Signaling by TLR3 was determined by the amount of IL-6 secreted in the cell culture media. A control siRNA had no effect on WT LL-37/poly(I:C) enhancement of IL-6 production. Pentamide or LL8-37 added along with LL-37 had no effect on IL-6 production unless FPRL-1 expression was reduced. Interestingly, the addition of Peptide A and LL-29 along with LL-37 resulted in a reduction in IL-6 levels whether the cells were treated with a siRNA to FPRL-1 or a nonspecific control. These results suggest that LL-29 and Peptide A can antagonize LL-37 enhancement of TLR3 signaling in response to poly (I:C).

Example 10. LL-29 can Affect LL-37/Poly(I:C)'s Co-Localization with TLR3 in BEAS-2B Cells In this example we establish that antagonists of LL-37 oligomerize with native LL-37 and deplete the native LL-37 from double strand nucleotides association and prevent TLR3's ligands (dsRNA) trafficking to endosome.

LL-29 does not use FPRL-1 to affect TLR3 signaling, but can bind LL-37 in vitro (FIG. 6B and Table 1). We examined whether it could prevent the trafficking of LL-37/poly(I:C) to endosomes that harbor TLR3. Confocal microscopy was used to examine the effect of LL-29 on the colocalization of LL-37/poly(I:C) with TLR3 in BEAS-2B cells. As expected, fLL-37 was found to colocalize with TLR3 while Sc-37 did not. However, the addition of LL-29 to fLL-37 and poly(I:C) reduced the co-localization between fLL-37 and TLR3 (FIGS. 7A and 7B).

These results suggest that LL-29 and its derivatives may prevent native LL-37 from engaging dsRNA, therefore, reducing the available ligands for TLR3 activation of pro-inflammatory signaling.

Example 11. Antimicrobial Activities of LL-37 and LL-29

In this example we sought to examine the antimicrobial activities of LL-37 and LL-29.

The standard Minimal inhibitory concentration (MIC) assay was used to examine the concentrations of antibiotics and peptides needed to kill *Escherichia coli* ATCC 25922. bacterial cultures were infused with LL-37 or LL-29 along with known antibiotics, doxorubicin, kanamycin, and trimethylprim to enable analysis of the synergistic effects of LL-37 and LL-29 with the antibiotics. LL-37 additively improved the MIC by 2-fold. Importantly, LL-29 improved the MIC by at least 4-fold with all three antibiotics. Thus, LL-29 can reduce activation of nucleic acid-induced innate immune responses, presumably by suppressing the signaling pathways of LL-37, as demonstrated in Examples 8-10. On the other hand, LL-29 retains the effective killing of the Gram-negative bacterium, *E. coli*.

TABLE 2

LL-29 can enhance the activities of antibiotics against *E. coli* ATCC 25922.

| Peptide (final Conc.) | Antibiotic | MIC (µg/ml) |
|---|---|---|
| None | Doxorubicin | 0.5 |
| None | Kanamycin | 4 |
| None | Trimethoprim | 0.25 |
| LL-37(10 µg/ml) | Doxorubicin | 0.25 |
| LL-37(10 µg/ml) | Kanamycin | 2 |
| LL-37(10 µg/ml) | Trimethoprim | 0.25 |
| LL-37(10 µg/ml) | None | growth |
| LL-29(10 µg/ml) | Doxorubicin | ≤0.06 |
| LL-29(10 µg/ml) | Kanamycin | ≤0.5 |
| LL-29(10 µg/ml) | Trimethoprim | ≤0.06 |
| LL-29(10 µg/ml) | None | growth |

This result suggest that although LL-37 and LL-29 both have antimicrobial effect that increased the efficacy of antibiotics, the synergistic effect LL-29 provided to these antibiotics greatly outperforms that from LL-37, indicating LL-29 possesses an advantage in microbial killing.

This provides a unique opportunity for LL-29 or any other LL-37 antagonists with similar function illustrated herein to be used as immune regulators that enhances preferred bacterial killing, but inhibit detrimental inflammatory responses triggered by bacterial infection.

Example 12. Other Antimicrobial Peptides

In this example, we sought to identify whether antimicrobial peptides produced by other mammals, LL-37 orthologs, could suppress the LPS-induced inflammatory response without activating the nucleic acid-induced inflammatory response.

Singh et al. (2012) had previously reported that the LL-37 ortholog from mouse, mCRAMP failed to activate cytokine production induced by TLR3 in both human and mouse cell lines. Herein, we analyzed the LL-37 orthologs from Rhesus monkeys, pig, sheep, guinea pigs, rabbit, as well as mouse (FIG. 14A). All peptides were chemically synthesized and assayed for the induction of inflammatory cytokine IL-6 in the presence of the double-stranded RNA mimic, poly(I:C) or the Reovirus dsRNA, Reo S4 (FIGS. 14B and 14C). As expected, mCRAMP was unable to enhance IL-6 production with either poly(I:C) or Reo S4. However, the peptides from pig (PAMP-37), sheep (SMAP-20), and rabbits (CAP-18) all failed to enhance signaling by poly(I:C) and Reo S4. These three peptides also failed to induce signaling by the ssDNA ligand for the Toll-like receptor 9, ODN2009 (FIG. 14D). Importantly, all LL-37 orthologs tested had the ability to reduce IL-6 production in response to LPS (FIG. 14E). Notably, the monkey and the guinea pig LL-37 ortholog, RL-37, had activities that are more similar to that of the human LL-37 (FIG. 14 B-E).

LL-37 uses the Formyl peptide receptor-like 1 (FPRL-1) receptor to deliver nucleic acids into endosomes, where activation of the Toll-like receptors that recognize nucleic acids takes place (Singh et al., 2014). We sought to determine whether the LL-37 orthologs from other mammals could also use the FPRL-1 in the human BEAS-2B cells to deliver dsRNA. BEAS-2B cells were treated with poly(I:C) along with the peptides and the peptides from pig, sheep, rabbit, and mouse had reduced ability to use the FPRL-1 to activate IL-6 production. Interestingly, the monkey and guinea pig peptides had activities more similar to the human LL-37 in the use of the FPRL-1 receptor for activation of IL-6 production.

Figure 8:
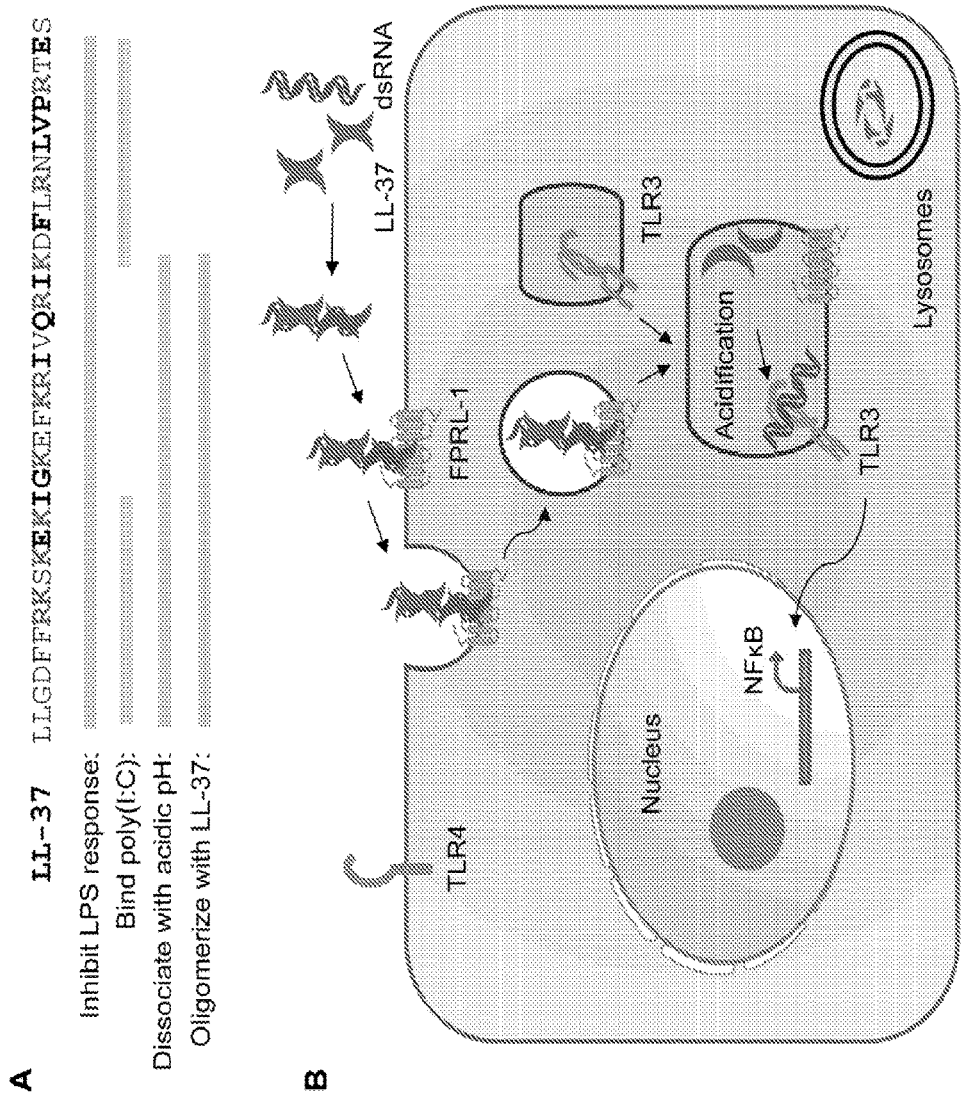
FIG. 8. A model for LL-37 enhancement of dsRNA-induced TLR3 signaling. A. Sequence of LL-37 (SEQ ID NO: 4) and summary of residues involved in LPS binding, poly(I:C) binding, pH dependent dissociation and oligomerization. B. Schematic of LL-37 mediated poly(I:C) signaling. LL-37 binds to dsRNA and is internalized to endosomes through the FPRL-1 receptor. After maturation, the acidic environment of endosomes dissociates dsRNA and LL-37. The dsRNA is then recognized by TLR3 for signaling while LL-37 is transferred to lysosomes and degraded.

These results from FIGS. 14 and 15, together with prior examples identified LL-37 antagonists, such as LL-29, peptide A and LL8-37 etc., indicate that these peptides retain LL-37's antimicrobial effect, yet abolish LL-37 enhanced autoimmune signaling. A schematic diagram of FIG. 8 provides a non-limiting theory, explaining the potential use of LL-29 and related mammalian antimicrobial peptides to balance inflammation caused by either bacterial or virus infection.

These and other features, aspects and advantages of the present invention will become better understood with reference to the following figures, associated descriptions and claims.

What is claimed is:

1. A composition comprising a peptide selected from the group consisting of SEQ ID NO: 1 (LL-29), SEQ ID NO: 2 (Peptide A), SEQ ID NO: 3 (LL8-37), SEQ ID NO: 22 (pig Proadrenomedullin Peptide (PAMP)-37), SEQ ID NO: 23 (sheep Myeloid Antimicrobial Peptide (SMAP)-29) and SEQ ID NO: 24 (rabbit Cationic Antimicrobial Peptide (CAP)-18), and an antibiotic, wherein the antibiotic is not attached to the peptide, and wherein the antibiotic is doxorubicin, kanamycin, or trimethoprim.

2. The composition according to claim 1, wherein said peptide abrogates LL-37 associated double-stranded nucleic acid trafficking to endosomes.

3. The composition according to claim 2, wherein said LL-37 associated double-stranded nucleic acid trafficking to endosomes is mediated by formyl peptide receptor like (FPRL)-1.

4. The composition according to claim 1, wherein said peptide inhibits toll-like receptor (TLR)-3 mediated autoimmune inflammatory response.

5. The composition according to claim 1, wherein the peptide is SEQ ID NO: 1 (LL-29).

* * * * *

SEQUENCE LISTING

```
<160> NUMBER OF SEQ ID NOS: 26

<210> SEQ ID NO 1
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: LL29

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg
            20                  25

<210> SEQ ID NO 2
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: peptide A

<400> SEQUENCE: 2

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Lys Leu Val
            20                  25                  30

Pro Gln Pro Glu Gln
        35

<210> SEQ ID NO 3
<211> LENGTH: 29
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: LL8-37

<400> SEQUENCE: 3

Ser Lys Glu Lys Ile Gly Lys Glu Phe Lys Arg Ile Val Gln Arg Ile
1               5                   10                  15

Lys Asp Phe Leu Arg Asn Leu Val Pro Arg Thr Glu Ser
            20                  25

<210> SEQ ID NO 4
<211> LENGTH: 37
<212> TYPE: PRT
<213> ORGANISM: Homo sapiens
```

```
<220> FEATURE:
<221> NAME/KEY: MISC_FEATURE
<222> LOCATION: (1)..(37)
<223> OTHER INFORMATION: LL37

<400> SEQUENCE: 4

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 5
<211> LENGTH: 21
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: LL9-29

<400> SEQUENCE: 5

Ser Lys Glu Lys Ile Gly Lys Glu Phe Lys Arg Ile Val Gln Arg Ile
1               5                   10                  15

Lys Asp Phe Leu Arg
            20

<210> SEQ ID NO 6
<211> LENGTH: 34
<212> TYPE: PRT
<213> ORGANISM: Mus sp.
<220> FEATURE:
<221> NAME/KEY: MISC_FEATURE
<222> LOCATION: (1)..(34)
<223> OTHER INFORMATION: mCRAMP

<400> SEQUENCE: 6

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 7
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: pentamide

<400> SEQUENCE: 7

Leu Leu Gly Asn Phe Phe Arg Lys Ser Lys Gln Lys Ile Gly Lys Gln
1               5                   10                  15

Phe Lys Arg Ile Val Gln Arg Ile Lys Asn Phe Leu Arg Asn Leu Val
            20                  25                  30

Pro Arg Thr Gln Ser
            35
```

<210> SEQ ID NO 8
<211> LENGTH: 7
<212> TYPE: PRT
<213> ORGANISM: Homo sapiens

<400> SEQUENCE: 8

Leu Leu Gly Asp Phe Phe Arg
1               5

<210> SEQ ID NO 9
<211> LENGTH: 8
<212> TYPE: PRT
<213> ORGANISM: Homo sapiens

<400> SEQUENCE: 9

Leu Leu Gly Asp Phe Phe Arg Lys
1               5

<210> SEQ ID NO 10
<211> LENGTH: 10
<212> TYPE: PRT
<213> ORGANISM: Homo sapiens

<400> SEQUENCE: 10

Leu Leu Gly Asp Phe Phe Arg Lys Ser Lys
1               5                   10

<210> SEQ ID NO 11
<211> LENGTH: 12
<212> TYPE: PRT
<213> ORGANISM: Homo sapiens

<400> SEQUENCE: 11

Leu Leu Gly Asp Phe Phe Arg Lys Ser Lys Glu Lys
1               5                   10

<210> SEQ ID NO 12
<211> LENGTH: 18
<212> TYPE: PRT
<213> ORGANISM: Homo sapiens

<400> SEQUENCE: 12

Leu Leu Gly Asp Phe Phe Arg Lys Ser Lys Glu Lys Ile Gly Lys Glu
1               5                   10                  15

Phe Lys

<210> SEQ ID NO 13
<211> LENGTH: 19
<212> TYPE: PRT
<213> ORGANISM: Homo sapiens

<400> SEQUENCE: 13

Leu Leu Gly Asp Phe Phe Arg Lys Ser Lys Glu Lys Ile Gly Lys Glu
1               5                   10                  15

Phe Lys Arg

<210> SEQ ID NO 14
<211> LENGTH: 23
<212> TYPE: PRT
<213> ORGANISM: Homo sapiens

<400> SEQUENCE: 14

Leu Leu Gly Asp Phe Phe Arg Lys Ser Lys Glu Lys Ile Gly Lys Glu
1               5                   10                  15

Phe Lys Arg Ile Val Gln Arg
            20

<210> SEQ ID NO 15
<211> LENGTH: 7
<212> TYPE: PRT
<213> ORGANISM: Homo sapiens

<400> SEQUENCE: 15

Ile Gly Lys Glu Phe Lys Arg
1               5

<210> SEQ ID NO 16
<211> LENGTH: 10
<212> TYPE: PRT
<213> ORGANISM: Homo sapiens

<400> SEQUENCE: 16

Ile Val Gln Arg Ile Lys Asp Phe Leu Arg
1               5                   10

<210> SEQ ID NO 17
<211> LENGTH: 11
<212> TYPE: PRT
<213> ORGANISM: Homo sapiens

<400> SEQUENCE: 17

Ile Lys Asp Phe Leu Arg Asn Leu Val Pro Arg
1               5                   10

<210> SEQ ID NO 18
<211> LENGTH: 14
<212> TYPE: PRT
<213> ORGANISM: Homo sapiens

<400> SEQUENCE: 18

Ile Lys Asp Phe Leu Arg Asn Leu Val Pro Arg Thr Glu Ser
1               5                   10

<210> SEQ ID NO 19
<211> LENGTH: 8
<212> TYPE: PRT
<213> ORGANISM: Homo sapiens

<400> SEQUENCE: 19

Asn Leu Val Pro Arg Thr Glu Ser
1               5

<210> SEQ ID NO 20
<211> LENGTH: 37
<212> TYPE: PRT
<213> ORGANISM: Macaca mulatta
<220> FEATURE:
<221> NAME/KEY: MISC_FEATURE
<222> LOCATION: (1)..(37)
<223> OTHER INFORMATION: Monkey RL-37

```
<400> SEQUENCE: 20

Arg Leu Gly Asn Phe Phe Arg Lys Val Lys Glu Lys Ile Gly Gly
1               5                   10                  15

Leu Lys Lys Val Gly Gln Lys Ile Lys Asp Phe Leu Gly Asn Leu Val
                20                  25                  30

Pro Arg Thr Ala Ser
            35

<210> SEQ ID NO 21
<211> LENGTH: 43
<212> TYPE: PRT
<213> ORGANISM: Cavia sp.
<220> FEATURE:
<221> NAME/KEY: MISC_FEATURE
<222> LOCATION: (1)..(43)
<223> OTHER INFORMATION: Guinea Pig CAP-11

<400> SEQUENCE: 21

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
                20                  25                  30

Glu Tyr Gly Gln Ile Pro Tyr Pro Cys Arg Ile
            35                  40

<210> SEQ ID NO 22
<211> LENGTH: 37
<212> TYPE: PRT
<213> ORGANISM: Sus scrofa
<220> FEATURE:
<221> NAME/KEY: MISC_FEATURE
<222> LOCATION: (1)..(37)
<223> OTHER INFORMATION: Pig PMAP-37

<400> SEQUENCE: 22

Gly Leu Leu Ser Arg Leu Arg Asp Phe Leu Ser Asp Arg Gly Arg Arg
1               5                   10                  15

Leu Gly Glu Lys Ile Glu Arg Ile Gly Gln Lys Ile Lys Asp Leu Ser
                20                  25                  30

Glu Phe Phe Gln Ser
            35

<210> SEQ ID NO 23
<211> LENGTH: 29
<212> TYPE: PRT
<213> ORGANISM: Ovis sp.
<220> FEATURE:
<221> NAME/KEY: MISC_FEATURE
<222> LOCATION: (1)..(29)
<223> OTHER INFORMATION: Sheep SMAP-29

<400> SEQUENCE: 23

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
                20                  25

<210> SEQ ID NO 24
<211> LENGTH: 37
<212> TYPE: PRT
<213> ORGANISM: Unknown
<220> FEATURE:
<223> OTHER INFORMATION: Description of Unknown:
      rabbit CAP-18 sequence
```

```
<220> FEATURE:
<221> NAME/KEY: MISC_FEATURE
<222> LOCATION: (1)..(37)
<223> OTHER INFORMATION: Rabbit CAP-18

<400> SEQUENCE: 24

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 25
<211> LENGTH: 37
<212> TYPE: PRT
<213> ORGANISM: Homo sapiens

<400> SEQUENCE: 25

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Leu Lys Leu Arg Phe Glu Phe Ser Lys Ile Lys Gly Glu Phe Leu
1               5                   10                  15

Lys Thr Pro Glu Val Arg Phe Arg Asp Ile Lys Leu Lys Asp Asn Arg
            20                  25                  30

Ile Ser Val Gln Arg
        35
```